(12) United States Patent
Wang et al.

(10) Patent No.: US 9,790,551 B2
(45) Date of Patent: Oct. 17, 2017

(54) USE OF TRPC6 MRNA LEVELS IN PERIPHERAL BLOOD CELLS FOR EARLY DETECTION/DIAGNOSIS OF SENILE DEMENTIA

(71) Applicant: Aging Wise Biotechnology, Inc., Wuhu (CN)

(72) Inventors: Yizheng Wang, Shanghai (CN); Junfeng Wang, Shanghai (CN); Rui Lu, Shanghai (CN)

(73) Assignee: Aging Wise Biotechnology, Inc., Wuhu (CN)

( * ) Notice: Subject to any disclaimer, the term of this patent is extended or adjusted under 35 U.S.C. 154(b) by 0 days.

(21) Appl. No.: 14/765,715

(22) PCT Filed: Jan. 24, 2014

(86) PCT No.: PCT/CN2014/071325
§ 371 (c)(1),
(2) Date: Aug. 4, 2015

(87) PCT Pub. No.: WO2014/117680
PCT Pub. Date: Aug. 7, 2014

(65) Prior Publication Data
US 2016/0002725 A1    Jan. 7, 2016

(30) Foreign Application Priority Data
Feb. 4, 2013   (CN) .......................... 2013 1 0044282

(51) Int. Cl.
| *C12Q 1/68* | (2006.01) |
| *A61K 38/08* | (2006.01) |
| *A61K 38/57* | (2006.01) |
| *C07K 14/705* | (2006.01) |
| *A61K 38/17* | (2006.01) |

(52) U.S. Cl.
CPC ............ *C12Q 1/6883* (2013.01); *A61K 38/08* (2013.01); *A61K 38/177* (2013.01); *A61K 38/57* (2013.01); *C07K 14/705* (2013.01); *C12Q 2600/112* (2013.01); *C12Q 2600/158* (2013.01)

(58) Field of Classification Search
CPC ............ A61K 38/177; C12Q 2600/158; C12Q 1/6883; C12Q 2600/178; C12Q 1/6806; C12Q 1/6876; C12Q 1/68
See application file for complete search history.

(56) References Cited

U.S. PATENT DOCUMENTS

| 7,964,573 B2 * | 6/2011 | Remillard ............ C07K 14/705 424/184.1 |
| 2006/0257500 A1 | 11/2006 | Winn et al. |

FOREIGN PATENT DOCUMENTS

| CN | 1714101 A | 12/2005 |
| CN | 101948912 A | 1/2011 |
| CN | 102100913 A | 6/2011 |
| EP | 1527343 A2 | 5/2005 |
| KR | 2005-0075134 A | 7/2005 |
| WO | WO 2004/013629 A2 | 2/2004 |
| WO | WO 2005/074923 A1 | 8/2005 |
| WO | WO 2005/119262 A2 | 12/2005 |

OTHER PUBLICATIONS

Griffith et al., Neurobiological effects of Hyperforin and its potential in Alzheimer's disease therapy. Curr Med Chem. 2010;17(5):391-406. Review.
Cui et al., the TRPC6 Ion Channel in Central Nervous System. Chinese J Neuroanatomy. Dec. 2011;27(31):565-570.

* cited by examiner

*Primary Examiner* — Gregory S Emch
(74) *Attorney, Agent, or Firm* — Wolf, Greenfield & Sacks, P.C.

(57) ABSTRACT

The invention relates to the use of TRPC6 mRNA levels in peripheral blood cells for the early detection/diagnosis of senile dementia. Specifically, the present invention provides a classic transient receptor potential channel 6 (TRPC6) gene or protein thereof and the use of same in preparing a reagent or test kit for detecting or diagnosing Alzheimer's disease. The present invention further relates to a polypeptide used to prepare a medicament that treats AD, and relates to a composition of said polypeptide.

4 Claims, 8 Drawing Sheets

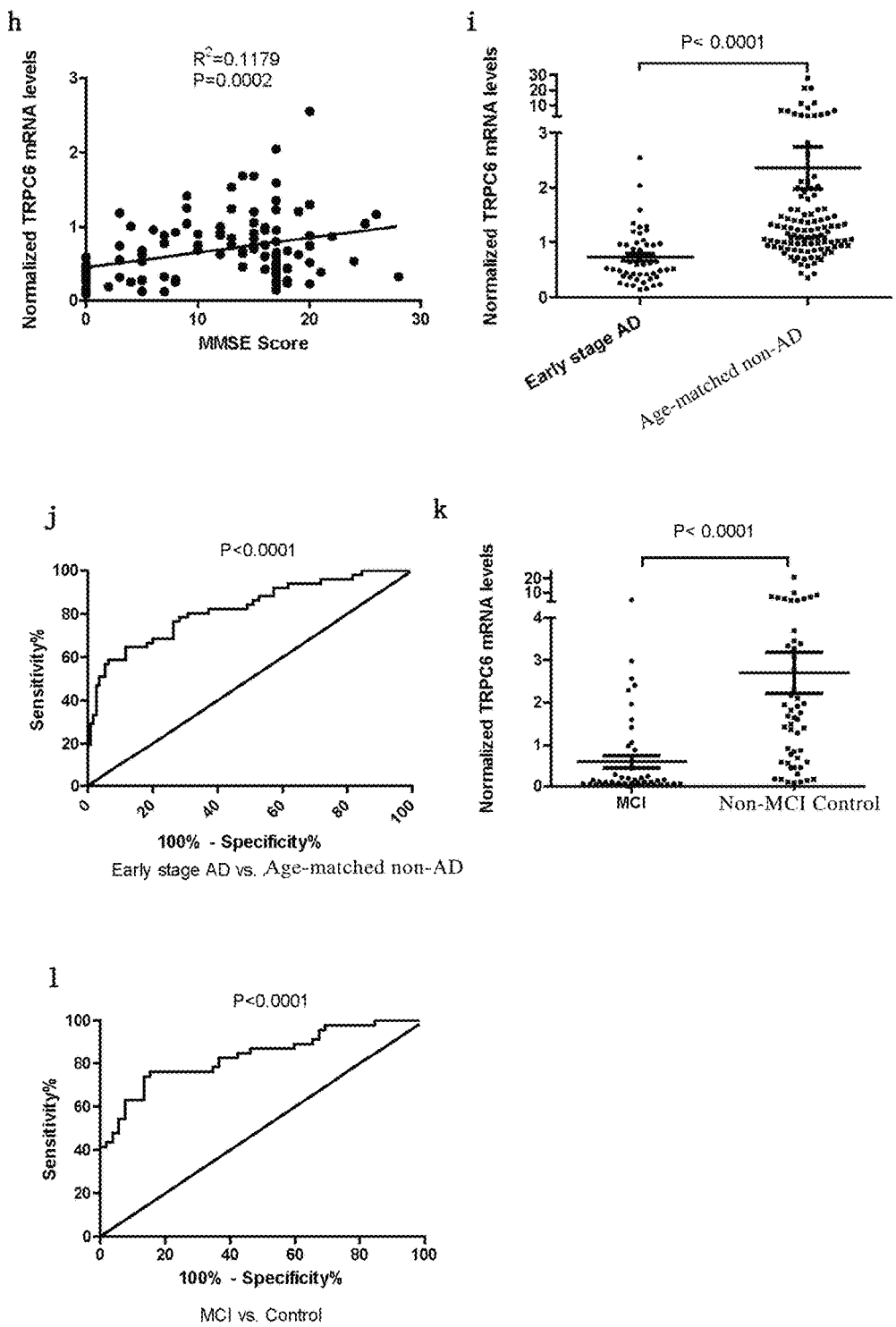
Figure 1 (continue)

```
        Homo sapiens  488-508: TSCFSWMEMLIISWVIGMIWA
        Mus musculus  487-507: TSCFSWMEMLIISWVIGMIWA
                 Rat  487-507: TSCFSWMEMLIISWVIGMIWA
       Pan troglodytes 488-508: TSCFSWMEMLIISWVIGMIWA
           Bos taurus  488-508: TSCFSWMEMLIISWVIGMIWA
Canis lupus familiaris  489-509: TSCFSWMEMLIISWVIGMIWA
          Felis catus  435-455: TSCFSWMEMLIISWVIGMIWA
```

USE OF TRPC6 MRNA LEVELS IN PERIPHERAL BLOOD CELLS FOR EARLY DETECTION/DIAGNOSIS OF SENILE DEMENTIA

RELATED APPLICATIONS

This application is a national stage filing under 35 U.S.C. §371 of International Application PCT/CN2014/071325 entitled "USE OF TRPC6 MRNA LEVELS IN PERIPHERAL BLOOD CELLS FOR EARLY DETECTION/DIAGNOSIS OF SENILE DEMENTIA" filed Jan. 24, 2014, which claims priority to CN Application No. 201310044282.0, filed Feb. 4, 2013, the entire disclosure of each of which is incorporated by reference in its entirety.

TECHNICAL FIELD

The present invention relates to the biotechnology field, specifically, relates to the use of Transient Receptor Potential Canonical 6 (TRPC6) gene or protein thereof, for preparing the reagent or kit for the prediction or diagnosis of Alzheimer disease (AD). The present invention also relates to a polypeptide and composition thereof for preparing a medicament for treating AD.

BACKGROUND

Alzheimer's disease, namely senile dementia, is the most common neurodegenerative disease leading to dementia in the aged. According to a report by John Hopkins University (US), 1 of 85 people would be living with AD by 2050. The clinical manifestations of AD are progressive loss of memory and cognitive function, decline of daily self-care ability, and emergence of various psychotic symptoms and behavior disorders. The autopsied brain tissue sections of AD victims are characterized by extracellular senile plaques and intracellular neurofibrillary tangles. Wherein, senile plaques are mainly composed of neurotoxic βamyloid (Aβ) peptide, which is proposed to be responsible for AD pathogenesis in the mainstream theory of 'Amyloid Hypothesis'.

Further, Aβ is generated through a sequential cleavage of Amyloid Precursor Protein (APP) by β- and γ-secretase, while the α-secretase cleavage of APP precludes Aβ formation and produces neurotrophic sAPPα (Mudher, A. & Lovestone, S. Trends Neurosci 25, 22-26 (2002); Selkoe, D. J. Ann Intern Med 140, 627-638 (2004); Selkoe, D. J. Nat Med 17, 1060-1065).

As to the diagnosis of AD, the golden standard of AD diagnosis presently relys on the pathological examination of postmortem brain section from the victims to confirm the existence of extracellular plaques and intracellular tangles. Instead, the clinical diagnosis of AD relys on the examining of cognitive function with tests such as mini-mental state examination (MMSE). However, as a subjective test for diagnostic basis, the specificity and the sensitivity of MMSE are low.

However, an early prediction of AD risk and an early intervention obviously are more clinically valuable than a late diagnosis after cognitive impairment or a postmortem diagnosis.

Therefore, there is an urgent need for the field to develop a sensitive, reliable biomarker suitable for early AD prediction/diagnosis so as to identify high-risk patients objectively and accurately before cognitive impairments happens, predict the possibility of AD at early stage, and provide a time window for the prevention or treatment of AD.

As to the AD treatment, it is known that the regulation of APP cleavage by secretases (such as γ-secretase) for reducing Aβ production can be utilized for AD treatment. However, clinical trials for treating AD by using γ-secretase inhibitor turned out to be unsuccessful. According to the present main view, the failure of the clinical trials was attributed to the diverse substrates of γ-secretase besides APP, such as Notch, E-cadherin and ErbB-4, etc (Haapasalo, A. & Kovacs, D. M. *J Alzheimers Dis* 25, 3-28; Xia, W. & Wolfe, M. S. *J Cell Sci* 116, 2839-2844 (2003)). These substrates achieve their important physiological functions through γ-secretase cleavage. Therefore, γ-secretase inhibitors may interfere the nomal physiological functions of many substrates.

Recently, Eli Lily terminated a phase 3 clinical trial of a γ-secretase inhibitor (Semagacestat, LY450139). The clinical result showed that after taking Semagacestat, the cognitive function of the AD patients was declined, and the risk of skin cancer and the adverse gastrointestinal reaction were increased. Wherein, the latter two were considered to be related with the disadvantaged inhibition of γ-secretase cleavage of Notch (Siemers, E., et al. Safety, *Clin Neuropharmacol* 28, 126-132 (2005); Siemers, E. R., et al. *Neurology* 66, 602-604 (2006); Hofmann, T., Schaefer, M., Schultz, G. & Gudermann, T. *Proc Natl Acad Sci USA* 99, 7461-7466 (2002).). This indicated that a desired medication for AD treatment must specifically reduce the γ-secretase cleavage of APP without affecting its function for cleavage of other substrates.

Thus, it's still urgent to develop a medication for treating or preventing AD with fewer side effects.

SUMMARY OF THE INVENTION

One object of the present invention is to provide a specific, reliable biomarker for early prediction or diagnosis of AD and use thereof for AD prediction or diagnosis.

Another object of the present invention is to provide a therapeutic agent with fewer side effects for AD treatment or prevention and use thereof.

The first aspect of the present invention is providing a use of transient receptor potential canonical 6 (TRPC6) gene and/or protein thereof, for preparing reagent or kit for AD prediction or diagnosis through detection.

In another preferred embodiment, said TRPC6 gene includes DNA sequence or mRNA sequence.

In another preferred embodiment, said detection refers to the detection of TRPC6 mRNA level in peripheral blood cells.

In another preferred embodiment, said TRPC6 is derived from mammal, preferably, from human, mouse or rat.

In another preferred embodiment, said reagents include primers, probes, nucleic acid chip, protein chip or antibodies specific to TRPC6.

In another preferred embodiment, said primers are the primer pair as set forth by SEQ ID NO.: 1 (sense) and SEQ ID NO.: 2 (anti-sense).

The second aspect of the present invention is to provide a kit for AD prediction or diagnosis via detecting TRPC6 mRNA level in peripheral blood cells, said kit comprises nucleic acid chip for TRPC6 detection or primers for specific amplification of TRPC6 mRNA or cDNA, and instructions; wherein, said instruction includes following description: predicting or diagnosing AD via detecting TRPC6 mRNA level in peripheral blood cells.

In another preferred embodiment, said kit further comprises one or more reagents selected from the group consisting of:
(i) reagent(s) for extracting total RNA from peripheral blood cells;
(ii) primer(s) for reverse transcription;
(iii) reverse transcriptase(s) for reaction of reverse transcription;
(iv) polymerase(s) for PCR reaction.

The third aspect of the present invention is providing a use of a reagent for detecting TRPC6 mRNA for preparing a kit for early AD prediction or diagnosis via detecting expression levels of TRPC6 mRNA in peripheral blood cells.

In another preferred embodiment, said early refers to prediction or diagnosis of early AD patients (such as MCI patients), wherein, said early AD patients refer to patients with MMSE>15.

In another preferred embodiment, said MCI patients refer to patients with mild cognitive impairment but do not reach AD diagnostic criteria.

In another preferred embodiment, said detecting includes detecting expression levels of TRPC6 mRNA level in peripheral blood cells and comparing said level with normal control (or that of normal population).

In another preferred embodiment, said reagents comprise primers, probes, nucleic acid chip or protein chip.

The fourth aspect of the present invention is providing a detection method comprising steps:
(a) extracting mRNA in peripheral blood or peripheral blood cells from a detection object;
(b) detecting expression levels of TRPC6 mRNA level and comparing said level with that of normal population; if said expression levels are significantly lower than those of normal population, it suggests a higher risk or susceptibility of AD of said object than normal population.

In another preferred embodiment, said detecting refers to a real-time fluorescence quantitative PCR detecting.

The fifth aspect of the present invention is providing a use of TRPC6 protein or derivatives thereof or agonists thereof, for (a) preparing a medication for preventing and/or treating AD; (b) preparing a medication for reducing β-Amyloid peptide level; and/or (c) preparing activity modulator (especially a selective inhibitor) for γ-secretase.

In another preferred embodiment, for preparing a medication for reducing β-Amyloid peptide production level in neurons.

In another preferred embodiment, said TRPC6 protein is derived from mouse, preferably, the amino acid sequence is as set forth by SEQ ID NO.: 5.

In another preferred embodiment, said derivative protein is selected from the group consisting of:
(a) a polypeptide consisted of an amino acid sequence comprising the 487507aa of TRPC6 protein;
(b) a fusion protein formed by polypeptide (a) and an element of cell-penetrating peptide;
(c) a derivative polypeptide, which is derived from polypeptide (a) or (b) by addition, deletion, or alteration of one or more amino acid residue(s), and said derivative polypeptide has the activity of down-regulating Aβ level without affecting the function of γ-secretase for Notch cleavage;
(d) a polypeptide having an amino acid sequence corresponding to TM2 domain (487-507aa) of TRPC6 protein or a fusion protein formed by TM2 domain and an element of cell-penetrating peptide, and said polypeptide or said fusion protein (d) has the activity of down-regulating Aβ level without affecting the function of γ-secretase for Notch cleavage.

The sixth aspect of the present invention is providing an isolated polypeptide, said polypeptide is selected from the group consisting of:
(a) a polypeptide consisted of an amino acid sequence comprising the 487-507aa of TRPC6 protein;
(b) a fusion protein formed by polypeptide (a) and an element of cell-penetrating peptide;
(c) a derivative polypeptide, which is derived from polypeptide (a) or (b) by addition, deletion, or alteration of one or more amino acid residue(s), and said derivative polypeptide has the activity of down-regulating Aβ level without affecting the function of γ-secretase for Notch cleavage;
(d) a polypeptide having an amino acid sequence corresponding to TM2 domain (487-507aa) of TRPC6 protein or a fusion protein formed by TM2 domain and an element of cell-penetrating peptide, and said polypeptide or said fusion protein (d) has the activity of down-regulating Aβ level without affecting the function of γ-secretase for Notch cleavage.

In another preferred embodiment, the amino acid sequence of said polypeptide is as set forth by SEQ ID NO.:4.

The seventh aspect of the present invention is providing a polynucleotide encoding the polypeptide according to the sixth aspect of the present invention.

In another preferred embodiment, the sequence of said polynucleotide is as set forth by position 1459-1521 of SEQ ID NO.: 3.

The eighth aspect of the present invention is providing a vector containing the polynucleotide according to the seventh aspect of the present invention.

The ninth aspect of the present invention is providing a host cell, said cell contains the vector according to the eighth aspect of the present invention, or genome of said cell is integrated with exogenous polynucleotide according to the seventh aspect of the present invention.

The tenth aspect of the present invention is providing a method for producing the polypeptide according to the sixth aspect of the present invention, said method comprises:
(i) culturing said host cell according to the ninth aspect of the present invention so as to express the polypeptide according to the sixth aspect of the present invention; and
(ii) isolating said polypeptide according to the sixth aspect of the present invention from a culture system.

The eleventh aspect of the present invention is providing a pharmaceutical composition, comprising a pharmaceutically acceptable carrier and the polypeptide according to the sixth aspect of the present invention.

The twelfth aspect of the present invention is providing a use of the polypeptide according to the sixth aspect of the present invention, the polynucleotide according to the seventh aspect of the present invention, the vector according to the eighth aspect of the present invention or pharmaceutical composition according to the eleventh aspect of the present invention, for (a) preparing a medication for preventing and/or treating AD; (b) preparating a medication for reducing β-Amyloid peptide level; and/or (c) preparing an activity modulator (especially a selective inhibitor) for γ-secretase.

The thirteenth aspect of the present invention is providing a method for screening compound(s) for AD prevention or treatment, comprising steps of:
(a) for a testing group, adding a testing compound into the cell culture system, and observing TRPC6 expression levels and/or activity in the cells of the testing group; for a control group, adding no testing compound into the same cell culture system, and observing TRPC6 expression levels and/or activity in the cells of the control group;

wherein, if the TRPC6 expression levels and/or activity in cells of the testing group are higher than that in the cells of the control group, it indicated that said testing compound is a candidate compound for AD prevention or treatment with an effect of enhancing the expression levels and/or activity of TRPC6.

In another preferred embodiment, said method further comprises steps of:

(b) further determining the inhibition effect of the candidate compound obtained in step (a) on Aβ.

The fourteenth aspect of the present invention is providing a method for preventing or treating AD and/or MCI by administering the polypeptide according to claim 9 or the pharmaceutical composition according to claim 14 with a safe and effective amount to an object in need.

In another preferred embodiment, said AD includes early AD (MMSE>15).

It should be understood that in the present invention, the technical features specifically described above and below (such as in the Examples) can be combined with each other, thereby constituting a new or preferred technical solution which needs not be described one by one.

DESCRIPTION OF FIGURES

Wherein, FIG. 1a: TRPC6 mRNA levels in the peripheral blood cells of AD patients are significantly lower compared with those of age-matched non-AD controls. However, there is no difference in the TRPC6 mRNA levels between age-matched non-AD control group and young non-AD control group;

FIG. 1b: there is no significant difference in the TRPC5 mRNA levels among AD group, age-matched non-AD control group and young non-AD control group;

FIG. 1c: there is no significant difference in the TRPC6 mRNA levels between PD patients and age-matched non-PD control group;

FIGS. 1d, f and g: the results from larger sample size are quite similar to those in FIG. 1a, b and c.

FIG. 1e shows in the ROC curve analysis, AUC=0.8324, sensitivity=78.74%, specificity=71.82%. It indicated that high sensitivity and specificity could be reached when TRPC6 mRNA levels are used to distinguish AD from age-matched non-AD control group.

FIG. 1h shows the linear-regression analysis of TRPC6 mRNA and MMSE with a result of R2=0.1179, P=0.0002. It could be concluded that AD patients with severer dementia have lower TRPC6 mRNA levels in the peripheral blood cells.

FIG. 1i shows that TRPC6 mRNA levels in the peripheral blood cells of early-stage AD patients were significantly lower than those of age-matched non-AD control group (P<0.0001).

FIG. 1j: the ROC curve analysis shows: AUC=0.8235, sensitivity=78.43%, specificity=70.91%. It could be indicated that early-stage AD patients can be effectively diagnosed by using TRPC6 mRNA levels.

FIG. 1k shows that TRPC6 mRNA levels in the peripheral blood cells of MCI patients are significantly lower than those of age-matched non-MCI control group (***P<0.0001).

FIG. 1l: the ROC curve analysis shows AUC=0.8370, sensitivity=76.79%, specificity=84.62%. It could be concluded that MCI patients can be effectively diagnosed by using TRPC6 mRNA levels.

FIGS. 2a and 2b: the enhancement of Aβ accumulation by APP expression in HEK293 cells dose not affect the mRNA or protein levels of TRPC6 and TRPC5;

FIGS. 2c and 2d: there is no significantly difference in the mRNA levels of TRPC6 and TRPC5 in the peripheral blood cells or brain tissues between WT and APP/PS1 mice;

FIG. 2e: there is no difference in TRPC6 protein levels in brain tissue between WT and APP/PS1 mice.

FIG. 3a: ELISA shows that overexpressing TRPC6 in HEK293APP cells reduces Aβ levels, while overexpressing TRPC5 does not have such effect;

FIG. 3b, ELISA results show that RNAi knockout of TRPC6 in primary cultured cortical neurons enhances Aβ levels.

FIG. 3c, ELISA results show that RNAi knockout of TRPC6 in primary cultured cortical neurons enhanced Aβ levels, while knockout of TRPC5 does not have such effect.

FIG. 4a: Representative figures of senile plaques in the brain sections of APP/PS1 and APP/PS1/TRPC6 mice stained with Aβ antibody. Scale bar=500 um;

FIG. 4b, quantitative analysis of senile plaque load shows that the percentage of area loaded with plaque in brain sections from APP/PS1/TRPC6 mice is significantly lower than that from APP/PS1 mice;

FIG. 4c~e:ELISA results show that total level of Aβ, TBST-soluble and insoluble Aβ in APP/PS1/TRPC6 mice is significantly lower than that in APP/PS1 mice.

FIG. 5a: ELISA results show that overexpressing TRPC6 in C0S7C99 stable cells decreases Aβ levels;

FIG. 5b: overexpressing of TRPC6 in HEK293APP cells reduces C99GVP/UAS-luciferase activity induced by γ-secretase cleavage.

FIG. 5c: immunoblotting results show that overexpressing of TRPC6 does not affect NICD levels induced by γ-secretase cleavage of NotchΔE-myc.

FIG. 6a: the topological structure of TRPC6, with 6 transmembrane domains and cytoplasmic N- and C-terminals;

FIG. 6b: ELISA results show that overexpressing TRPC6-1/405 or TRPC6-725/930 does not affect Aβ levels;

FIG. 6c: demonstration of TRPC6 truncations;

FIG. 6d: ELISA results show that overexpressing variants containing 437-508aa of TRPC6 could reduce Aβ levels, while overexpressing variants without 437-508aa of TRPC6 could not reduce Aβ levels, indicating the 437-508aa is essential for TRPC6 to reduce Aβ levels;

FIG. 6e: ELISA results showed that TAT-TM2 fusion protein dose-dependently reduces Aβ levels in HEK293 cells;

FIG. 6f: immunoblotting shows that TAT-TM2 could not affect NICD production induced by γ-secretase cleavage of NotchΔE-myc;

FIG. 6g shows the schematic diagram of the structure of TRPC6 variants with mutations in TM2 (487-507aa);

FIG. 6h shows that a plasmid of TRPC6 with mutation in TM2 (487-507aa) domain could not reduce Aβ levels.

DETAILED DESCRIPTION OF THE INVENTION

Figure 1:
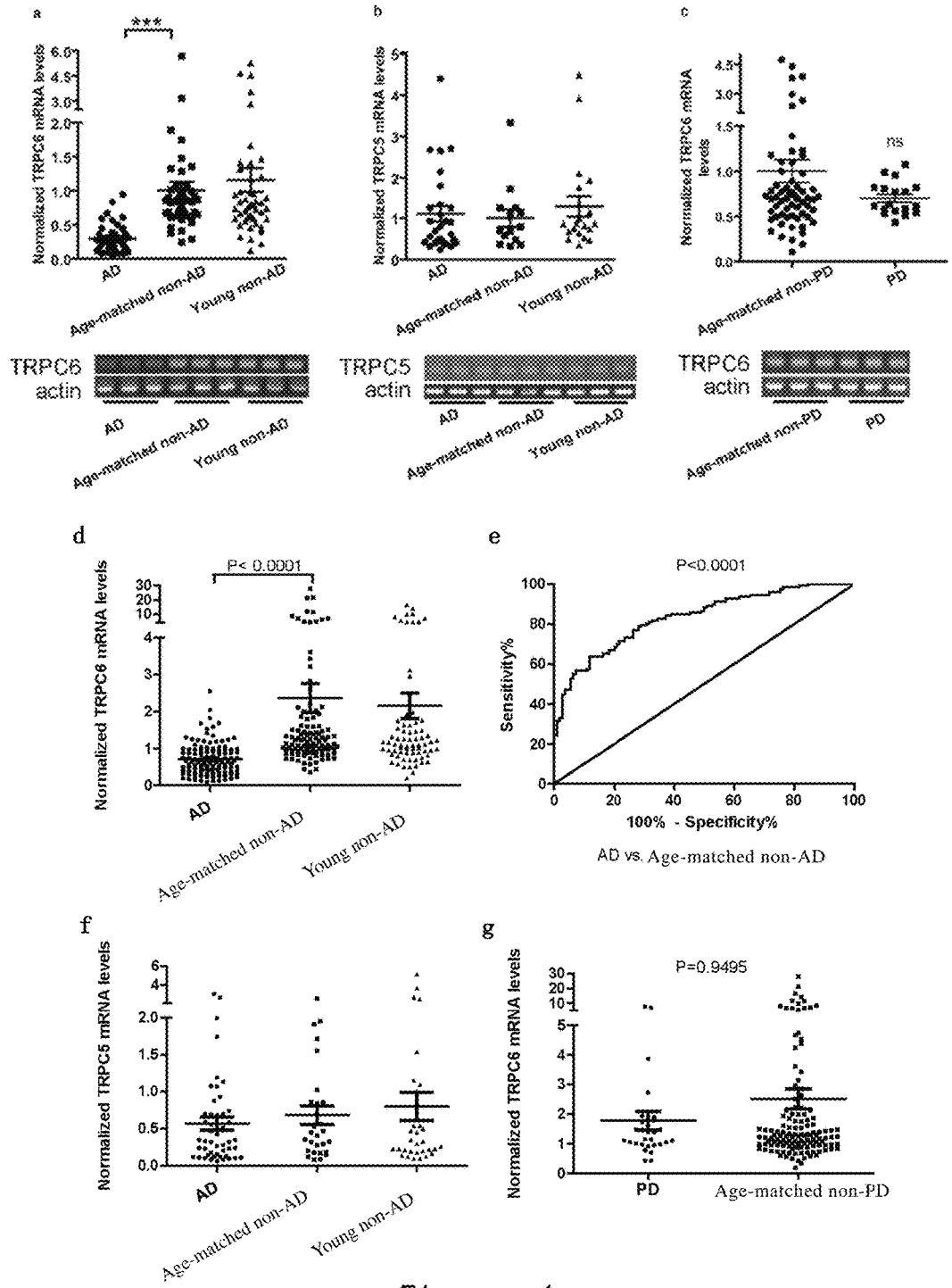
FIG. 1 shows the mRNA levels of TRPC6 and TRPC5 in the peripheral blood cells from different populations.

Upon long-term and intensive studies, the inventors surprisingly and firstly found out: the expressing level of TRPC6 mRNA in peripheral blood cells from AD patients is very low and it does not reduce with aging. Therefore, TRPC6 mRNA level in peripheral blood cell is strongly relevant with AD attack (or susceptibility) and it can be used as biomarker for predicting or diagnosing AD at early stage.

Moreover, for the first time, the inventors have proven: the amino acid sequence derived from 488-508aa of human TRPC6 protein or 487-507aa of mouse TRPC6 protein or TRPC6 fragment or mutated protein peptide containing the amino acid sequence can specifically reduce Aβ level so as to relieve AD symptoms with few side affect.

Based on the above works, the present invention is completed by the inventor.

TRPC6

TRPC6, transient receptor potential canonical 6 is a member of C (canonical) subfamily of TRP (transient receptor potential) gene superfamily. It encodes a non-selective cation channel which is permeable to calcium. TRPC6 mRNA could be detected in the brain tissue. Researches showed that TRPC6 plays certain roles in nervous development, learning and memory, and pain regulation.

Homologous or heterogeneous tetramer constitutes the functional TRPC6 ion channels which are permeable to $Na^+$, $K^+$ and $Ca^{2+}$. The N-terminal contains three anchor motifs which maybe relate to the membrane localization of the channels. There are conserved sequences in TRPC family of EWKFAR-box and two inositol triphosphate (IP3) receptor domains at the C-terminal; wherein, the second domain overlaps with a calmodulin (CaM) binding site.

TRPC6 is highly conserved among different species. TRPC6 used in the present invention can be derived from any mammal, including (but not limited to): human, rodent (such as mouse, rat), chimpanzee, bovine, canine or feline, etc. Further, TRPC6 includes wild type TRPC6, mutant type TRPC6 or its active fragments (such as TRPC6 mutant or active fragment containing 487-507aa). One of the nucleic acid sequence of wild type TRPC6 is as set forth by SEQ ID NO:3, which encodes the TRPC6 protein as set forth by SEQ ID NO.: 5.

The Use for Prediction or Diagnosis

The present invention provides a method for AD prediction or diagnosis (especially for early auxiliary prediction or diagnosis) or susceptibility thereof and a corresponding kit.

The relationship between the expression levels of TRPC (typically TRPC6) in peripheral blood cells from the detecting object and the AD risk is used in the method according to the present invention The research of the present invention indicated that the expression levels of some TRPC (such as TRPC5) are not related with AD risk. However, surprisingly, the expression levels of TRPC6 in peripheral blood cells (a non-brain tissue) are significantly related with AD risks, thereby particularly suitable for a biomarker for early auxillary prediction or diagnosis of AD.

The detecting method according to the present invention can be based on the expression levels of TRPC6 mRNA or the expression levels of TRPC6 protein.

According to the present invention, TRPC6 gene includes different nucleic acid sequences of TRPC6, such as DNA sequence or mRNA sequence.

A preferred detecting method is to detect the expression levels of TRPC6 mRNA in peripheral blood cells. A representative method comprises steps:

1) extracting mRNA in peripheral blood or peripheral blood cells from a detection object;
2) obtaining cDNA through reverse transcription;
3) conducting a real-time fluorescence quantitative PCR to the cDNA, obtaining a quantitative determination result of TRPC6 mRNA, and comparing the result with the expression levels of TRPC6 mRNA from normal population; if the result is significantly lower than that of normal population, it suggests that the AD risk or susceptibility of said object is higher than the AD risk or susceptibility of normal population.

TRPC6 Mutant or Active Fragment Containing 487-507aa

As used herein, the term "polypeptide" of the present invention refers to a class of polypeptides which are particularly useful. Said polypeptide corresponds to the active fragment ("core area" for short) of 487-507 amino acids (487-507aa) of TRPC6 from mouse as set forth by SEQ ID NO.: 4; or to a TRPC6 mutant containing said core area, or to a fusion protein, a derivative or an analog containing said core area.

As used herein, the terms "fragment" , "derivative" and "analog" refer to the polypeptides substantially maintaining the function or activity of inhibiting inflammation. The polypeptide fragments, derivatives or analogs of the present invention may be (i) a polypeptide with one or more conservative or non-conservative amino acid residues (preferably the conservative amino acid residues) being substituted, or (ii) a polypeptide having substituted group(s) in one or more amino acid residues, or (iii) a polypeptide formed by fusion of the polypeptide of the present invention with another compound (such as the compound that prolongs the half life of the polypeptide, such as polyethylene glycol), or (iv) a polypeptide with additional amino acid sequence fused to said polypeptide sequence (fusion proteins formed by fusion with leader sequence, secretion sequence or 6His tag sequence). According to the subject application, these fragments, derivatives and analogs are within the scope commonly known by the skilled person.

Figures 6, 7:
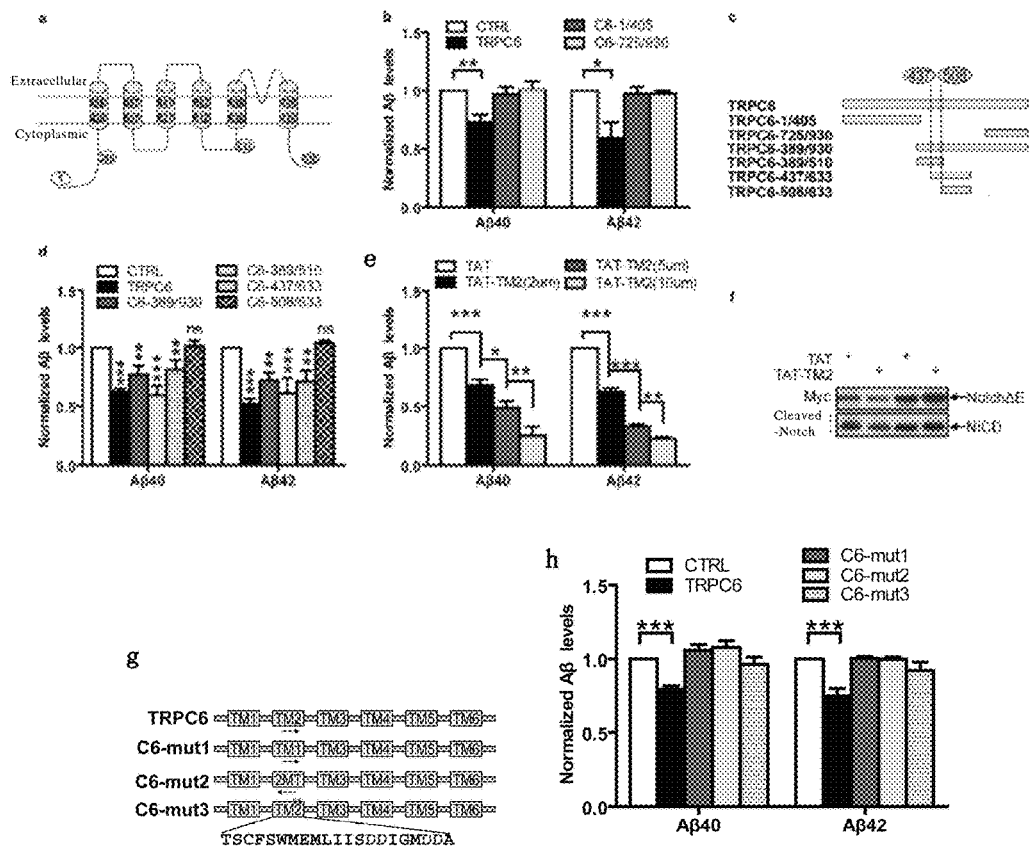
FIG. 6 shows the structure of TRPC6 and variants (or fragments) of TRPC6 containing 487-507aa could reduce Aβ levels.
FIG. 7 shows the alignment of TRPC6 protein sequences from *homo sapiens, Mus musculus, rattus norvegicus, pan troglodytes, bos taurus, canis lupus familiaris*, and *felis catus*.

FIG. 7 shows the corresponding position of the polypeptide of the present invention in TRPC6 protein from human, mouse, rat, chimpanzee, bovine, canine, and feline. It can be concluded that the polypeptide of the present invention is highly conserved in TRPC6 protein of many mammals.

A preferred polypeptide of the present invention is an active fragment containing the 487-507 amino acid sequence (487-507aa) of TRPC6 protein from mouse or an active fragment or protein having the corresponding 488-508 amino acid sequence of TRPC6 protein from human (as shown in FIG. 7). It should be understood, the length of the active fragment containing the above core area may be not limited to 21 amino acids. It can additionally comprise the flanking amino acid sequences derived from TRPC6 protein (such as TRPC6 proteins from human or nonhuman mammals). Generally, the length of said active fragment is 20-100, preferably 21-70, more preferably 21-40 amino acids. In the present invention, said active fragment does not include TRPC6 protein with full length.

The research of the present invention indicated that the polypeptide of the present invention can specifically inhibit the γ-secretase cleavage of APP, thereby effectively reducing Aβ levels and relieve AD symptoms. Furthermore, compared with the existing γ-secretase inhibitor, the great advantage of the polypeptide of the present invention is: it does not affect the function of γ-secretase cleavage of other substrates (such as Notch). Thus, it has few side effects.

APOE Gene

There are three alleles for human APOE gene: genotype of APOE2, APOE3 and APOE4. About 80% of population are APOE3 carriers while about 20% are APOE4 carriers. However, about 40-50% of sporadic AD patients are APOE4 carriers. Thus, APOE4 is considered to be the greatest risk factor in sporadic AD. In human body, liver produces APOE and release it into the blood. Then APOE could circulate around the body. Glia cells in the central nervous system also secrete APOE. The effect of APOE gene in AD is embodied in the normal physiological effect of APOE3, such as mediating Aβ clearance and degradation, and promoting neurite growth, etc. Once APOE is mutated into APOE4, these normal functions would be compromised, thereby increasing AD risk.

Pharmaceutical Composition and Therapeutical Use

The polypeptide or TRPC6 agonist (or activator) of the present invention can be directly used for disease treatment and prevention, eg. for AD prevention. When the polypeptide or TRPC6 agonist of the present invention is used, other therapeutical agents can be used at the same time.

When the polypeptide or TRPC agonist of the present invention is therapeutically used (administered), one or more following effects can be provided: (a) preventing and/or treating AD; (b) reducing β-amyloid protein levels; and/or (c) selectively inhibiting γ-secretase. Furthermore, the polypeptide or TRPC6 activator can gain good therapeutical effects with few side effects (for example, basically does not affect the function of γ-sectretase cleavage of other substrates.)

Generally, these substances can be prepared in the medium of non-toxic, inert and pharmaceutical acceptable aqueous carriers, wherein, pH generally is about 5-8, preferably pH is about 6-8 despite that pH value can varies with the characters of prepared substances and the diseases to be treated. The prepared pharmaceutical composition can be administered in conventional approaches comprising (but not limited to): intramuscular, intravenous, subcutaneous, intracutaneous, or topical administration. When TRPC6 agonist is a non-protein substance, it could be further administered orally.

The present invention further provides a pharmaceutical composition comprising the polypeptide of the present invention or the agonist thereof with safe and effective amounts and pharmaceutically acceptable carrier (s) or excipient(s). These carriers include (but are not limited to): saline, buffer solution, glucose, water, glycerol, ethanol, or the combination thereof. The pharmaceutical preparation should match the administration mode. The pharmaceutical composition of the present invention can be prepared into the form of injection, such as being prepared with saline or aqueous solution containing glucose or other auxiliaries by conventional methods. Pharmaceutical compositions, such as tablets and capsules can be prepared with conventional methods. Pharmaceutical compositions such as injections, solution, tablets and capsules may be preferably produced in sterile conditions. The administration amount of the active ingredients is a therapeutically effective amount, for example, about 1 μg/kg (body weight)-5 mg/kg (body weight) per day. Moreover, the polypeptide of the present invention can be further used with other therapeutical agents.

The polypeptide of the present invention or the agonist thereof is administered to mammals at a safe and effective dosage during the administration of said pharmaceutical composition; wherein, said safe and effective dosage generally is at least about 10 μg/kg (body weight), and at most circumstances it is no more than 8 mg/kg (body weight), preferably, said dosage is about 10 μg/kg (body weight)- about 1 mg/kg (body weight). Of course, factors such as administration route and health condition of patients should also be considered for the detailed dosage, which are within the technical scope of the skilled physicians.

The polynucleotide encoding the polypeptide of the present invention can be further used for treating or preventing purpose, such as by gene therapy method.

Medication Screening Method

The present invention further provides a medication screening method based on TRPC6. One of the method is:

firstly, screening for a compound affecting (increasing) the expression or activity of TRPC6, and then further testing the Aβ inhibition effect of the compound obtained by screening.

The method for screening candidate compound(s) for AD prevention or treatment according to the present invention is based on the impact on the expression levels and/or activity of TRPC6 of said compound. A typical screening method comprises steps of:

(a) for a testing group, adding a testing compound into the cell culture system, and observing TRPC6 expression levels and/or activity in the cells of the testing group; for a control group, adding no testing compound into the same cell culture system, and observing TRPC6 expression levels and/or activity in the cells of the control group;

wherein, if the TRPC6 expression levels and/or activity in cells of the testing group is higher than that in the cells of the control group, it indicated that said testing compound is a candidate compound for AD prevention or treatment with an effect of enhancing the expression levels and/or activity of TRPC6. And/or (b) further determining the inhibition effect of the candidate compound obtained in step (a) on Aβ. For example, for a testing group, adding a testing compound into the APP transfected cell culture system, and determing its Aβ inhibition effect; for a control group, adding no testing compound and determing Aβ inhibition effect; wherein, if Aβ levels of the testing group is lower than that of the control group, it indicated that said testing compound is a candidate compound for AD prevention or treatment.

Since the expression levels of TRPC6 is more related with Aβ reduction, therefore, the expression (levels) of TRPC6 is preferably determined.

The expression levels of TRPC6 can be tested on its mRNA level or protein level, for example, by conventional method or commercially available equipments and reagents (such as antibody, and primers, etc).

The Major Advantages of the Present Invention:

1. An objective biomarker existing in peripheral blood cells for early prediction or diagnosis of AD is provided for the first time. The present invention has firstly proved the significant relevance between TRPC6 mRNA in peripheral blood cells and AD risk, thereby confirming that TRPC6 mRNA levels in peripheral blood cells can be used as a biological foundation for AD diagnosis, and the subjectivity and uncertainty of MMSE indexes in clinical application can be avoided as well.

2. The time window of AD diagnosis is brought forward: the present invention determines TRPC6 mRNA directly in peripheral blood cells for AD prediction or early diagnosis and improved the prior art that can determine TRPC6 mRNA level only in brain tissues, thereby greatly advancing the time window of AD diagnosis and providing precious time for early intervention of AD prevention and treatment.

3. A major polypeptide for AD treatment is screened out: huge amounts of screenings and verifications have been conducted on cell and animal levels in the present invention. It has been proven that a core area consisted of 487-507aa is a major peptide for AD treatment, there by promoting the development of medications for AD treatment.

The invention is further illustrated by the following examples. These examples are only intended to illustrate the invention, but not to limit the scope of the invention. For the experimental methods in the following examples the specific conditions of which are not specifically indicated, they are performed under routine conditions, e.g., those described by Sambrook. et al., in Molecular Cloning: A Laboratory Manual, New York: Cold Spring Harbor Laboratory Press, 1989, or as instructed by the manufacturers. Unless otherwise specified, the percentage and portion refer to weight percentage and weight portion.

General Method

1. Total RNA Extraction of Peripheral Blood cells

The total RNA of peripheral blood cells were extracted with QIAamp® RNA Blood Mini Kit (QIAGEN Cat: 52304), and the experimental operations were performed according to its instructions as the following steps:

1) 5 volumes of Buffer EL were added into 1 volume of blood, the product was incubated for 10 min in ice-bath.

2) The product was centrifuged at 400×g for 10 min at 4° C. 2 volumes of Buffer EL were added for cells resuspension and for another centrifugation.

3) Buffer RLT was added and then the product was subjected to vibration for cell lysis.

4) The cell lysate was transformed into a QIA shredder spin column for centrifugation for 2 min at 16000×g.

5) 70% (volume) of ethanol was added for vibration.

6) The sample was pipetted into a QIAamp spin column for a 15 sec centrifugation at 8000×g.

7) 700 μl of Buffer RW1 was added to wash the column by a 15 sec centrifugation at 8000×g.

8) 500 μl of Buffer RPE was added for a 15 sec centrifugation at 8000×g.

9) 500 μl of Buffer RPE was added for centrifugation at 20,000×g for 3 min and then for centrifugation at 16000×g for 1 min.

10) 50 μl of RNase-free water was added for centrifugation at 8000×g for 1 min. The RNA was eluted into a 1.5 ml centrifuge tube.

2. Reverse Transcription 1) 10 ul of total RNA and 1 ul of random primers were added into the reaction system. The product was annealed for 5 min at 70° C. for the binding of the primers to the template.

2) Then, 4 ul of revertase Buffer, 0.5 ul of Ribolock RNase inhibitor, 1.5 ul RNase-free water, 2 ul of dNTPs and 1 ul of M-MLV Reverse Transcriptase was added into the reaction system. The product was vibrated to homogeneous and then for a short centrifugation, thereby obtaining the 20 ul reaction system. The reaction was set as followed: temp 25° C. for 10 min, 42° C. for 1 hr, 70° C. for 10 min and then the cDNA was obtained.

3. Real-time Fluorogenic Quantitative PCR

Reaction system was prepared as followed: 10 ul of 2×qPCR Master Mix, 4 ul of water, 5 ul of diluted cDNA and 1 ul of primer was added. The product was vibrated to homogeneous and then for a short centrifugation and then added in to a PCR reaction tube. The tube was placed into the qPCR amplifier and the following program was conducted: 95° C. for 2 min, 1 cycle→95° C., 10 s+63° C., 30 s, 40 cycles→95° C., and down to 60° C. for 1 cycle. Each sample was tested in triplicates to reduce operation error. The mixed solution was prepared first and then triplicated.

The sequences of TRPC6 primers areas set forth by SEQ ID NO.:1 (sense); SEQ ID NO.:2 (anti-sense).

The sequences of TRPC5 primers areas set forth by SEQ ID NO.:6 (sense); SEQ ID NO.:7 (anti-sense).

The sequences of actin primers areas set forth by SEQ ID NO.:8 (sense); SEQ ID NO.:9 (anti-sense).

4. Total RNA Extraction from Cells and Brain Tissues

Total RNA from cells and brain tissues was extracted with TRIzol® Reagent (Invitrogen Cat: 15596). The experimental operation was conducted according to its instructions as the following steps:

1) The cells or half brain with 1 ml Trizol were homogenized and then stilled in RNAse free EP tube for 5 minutes at room temperature.

2) 0.2 mL of chloroform was added in each EP. The product was shaken vigorously for 30 sec, stilled for 3 minutes at room temperature and centrifuged at 13200×g for 15 minutes at 4° C.

3) The mixture separated into 3 layers. The transparent aqueous phase was carefully transformed into a new 1.5 ml RNase free EP tube.

4) 0.5 mL of isopropanol was added in each EP. The product was shaked vigorously for 30 sec, stilled for 10 minutes at room temperature and centrifuged at 13200×g for 10 minutes at 4° C.

5) The supernatant was discarded. 1 mL of 75% ethanol was added into the EP tube, and the precipitation was dispersed and then centrifuged at 13200×g for 10 minutes at 4° C.

6) The supernatant was discarded. 1 mL of absolute ethanol was added into the EP tube, and the precipitation was dispersed and then centrifuged at 13200×g for 10 minutes at 4° C.

7) The supernatant was discarded. The precipitation was air-dried and 20 ul of RNase-free water was added to dissolve RNA.

5. Protein Extraction from Cells and Brain Tissues and WB Examination

Cells were lysed with SDS and the protein was denatured at 95° C. for 10 mins, thereby extracting the protein. Brain tissues were homogenized with RIPA and then conducted to rotation and mixing at 4° C. for 30 mins. After centrifuging at 4° C., 13,200×g, the supernatant was collected and denatured with SDS at 95° C. for 10 mins to extract the protein. The protein sample was separated by SDS-PAGE, and determined with TRPC6 (SAB, 1:300) and TRPC5 (Alomone, 1:200) antibodies.

6. Construction of APP/PS1 AD Mouse Models
  a) APP/PS1 mice (with B6C3 background) were purchased from Jackson laboratory (#004462).
  b) Construction of TRPC6 transgenic mouse The linearized plasmid containing the CaMKIIα promoter (8.5 kb upstream of the coding sequence) and mouse TRPC6 coding sequence was injected into the fertilized egg produced by the crossing of C57BL6 mouse and FBN mouse. The F1 offsprings were obtained and crossed with C57BL6 mice, and TRPC6 transgenic mice with pure C57BL6 background were obtained. CaMKIIα promoter drove TRPC6 expression in the forebrain excitatory neurons. The identification of the genotypes of TRPC6 transgenic mice was conducted by the primers as set forth by SEQ ID NO.:10 and SEQ ID NO.:11.

c) Wild type mice with C57 background were crossed with said APP/PS1 mice in 6.1, thereby obtaining the offsprings with C57 background. The APP/PS1 mice with C57 background were further crossed with TRPC6 transgenic mice. APP/PS1 and APP/PS1/TRPC6 mouse models were obtained in the offsprings.

7. Immunohistochemistry

Immunostaining of senile plaques was performed according to the instruction of VectaStain Universal ABC kit (VECTOR). Brain sections were first treated with $H_2O_2$ and antigen retrieved in formic acid. Upon blockage, the product was incubated with Aβ antibody 6E10 (purchased from COVANCE) overnight, then incubated with secondary antibody and ABC complex, and visualized with DAB (purchased from VECTOR) as a substrate. The brain sections were dehydrated, transparentized, sealed and then pictured with Neurolucidar.

8. Aβ Quantification

Upon collecting the culture medium of the cells, Aβ40 and Aβ42 levels were quantified with sandwich ELISA kit, respectively (purchased from Invitrogen). The forebrain of the mouse was dissected and separated, and then homogenized with GuHCL. After that, total Aβ was determined by ELISA. For determining TBST(Tris-Buffered Saline and 1% TritonX100, 1% SDS, 1% DOC) soluble and insoluble Aβ, upon TBST homogenation and centrifugation of the forebrain of the mouse, the supernatant was determined for TBST soluble Aβ by ELISA, and the precipitate was determined for TBST insoluble Aβ by ELISA upon another GuHCL homogenate.

9. Cell Cultures and Transfection.

HEK293APP stable cell line was cultured in DMEM culture solution (containing 200 ng/ml G418) with 10% FBS. COS7C99 cells were cultured in MEM/F12 culture solution (containing 0.4 ug/ml hygromycin B) with 5% FBS, 1% NEAA, and 200 mM Glutamax. All the transfection was conducted by using Lipofectamin 2000 (Invitrogen).

10. Luciferase Activity Assay

HEK293APP were transfected with C99-GVP/UASLuciferase, CTRL or TRPC6 plasmids, and were lysed 24 hours later. The luciferase activities were determined using the Luciferase assay system (purchased from Promega). β-gal was co-transfected to normalize the transfection efficiency.

11. Establishment of HEK293APP Stable Cells

HEK293 cells were inoculated to 60 mm dishes. When the density was close to 80%, 4 ug APP plasmid was transfected with Lipofectamine 2000. After 4 h, the culture medium was replaced and 400 ng/ml of G418 was added. Cells were passage 2 days later and G418 in the culture was maintained at 400 ng/ml. After 2-3 weeks, the cells not transected died gradually, and the survived cells were HEK293 cells expressing APP. Then, G418 was reduced to and maintained at 200 ng/ml.

EXAMPLE 1

Specific Detection of TRPC6 mRNA Levels in the Peripheral Blood Cells of AD Patients Blood samples (including patients and control) were collected from different hospitals and the groups were set as followed. Cell RNA was extracted and reverse-transcribed into cDNA. Real-time fluorescence quantitative PCR was performed for quantitative determination.

1.1 Comparision of TRPC6 mRNA Levels in the Peripheral Blood Cells among the Following Groups:
  a. sporadic AD (n=40, mean age=80.55±5.25)
  b. age-matched non-AD control (n=45, mean age=78.69±5.63)
  c. young non-AD control (n=45, mean age=60.6±6.56)

The results show: TRPC6 mRNA levels in the peripheral blood cells of AD patients were significantly lower than those of age-matched non-AD control group (***P<0.001; n=40-45). There is no significant difference in the TRPC6 mRNA levels between age-matched and young non-AD controls (n=45). See FIG. 1a.

The results from larger sample size are quite similar to those in FIG. 1a, b and c: see FIG. 1d, a. sporadic AD (n=127, mean age=80.5±5.7)

b. age-matched non-AD control (n=110, mean age=77.1±8.3)

c. young non-AD control (n=73, mean age=57.5±5.421)

In the ROC curve analysis, AUC=0.8324, sensitivity=78.74%, specificity=71.82%. See FIG. 1e.

1.2 Comparision of TRPC5 mRNA Levels in the Peripheral Blood Cells among the Following Groups:

a. sporadic AD (n=28, mean age=80.5±5.85)

b. age-matched non-AD control (n=14, mean age=70.07±8.25)

c. young non-AD control (n=20, mean age=57.45±5.36)

The results show that there is no difference in the TRPC5 mRNA levels among these three groups (n=14-28), see FIG. 1b.

The results from larger sample size are quite similar to those in FIG. 1a, b and c, see FIG. 1f:

a. sporadic AD (n=50, mean age=78.5±3.7)

b. age-matched non-AD control (n=28, mean age=75.4±5.3)

c. young non-AD control (n=34, mean age=56.5±4.1)

1.3 Comparision of TRPC6 mRNA Levels in the Peripheral Blood Cells among the Following Groups:

a. PD patients (Parkinson's Disease) for control (n=18, mean age=60±10.85);

b. age-matched non-PD control (n=62, mean age=64.08±8.01).

The results show that there is no difference in the TRPC6 mRNA levels in peripheral blood cells between PD patients and age-matched non-AD control group (n=18-62), see FIG. 1c.

The results from larger sample size are quite similar to those in FIG. 1a, b and c, see FIG. 1g:

a. PD (Parkinson's Disease) patients (n=30, mean age=65.2±2.5);

b. age-matched non-PD control (n=130, mean age=62.1±4.2)

1.4 Correlation between TRPC6 mRNA Levels in Peripheral Blood Cells of AD Patients and MMSE:

In order to analyze the correlation between TRPC6 mRNA levels in peripheral blood cells of AD patients and their dementia degree, linear-regression analysis was conducted for TRPC6 mRNA and MMSE and the result shows: R2=0.1179, P=0.0002, see FIG. 1h. It indicated that AD patients with more severe dementia have lower TRPC6 mRNA levels in peripheral blood cells.

1.5 Comparision of TRPC6 mRNA Levels in the Peripheral Blood Cells between the Following Groups:

a. early-stage AD (n=51, MMSE>15, mean age=74.3±3.2)

b. age-matched non-AD control (n=110, mean age=77.1±8.3)

The results show: TRPC6 mRNA levels in the peripheral blood cells of early-stage AD patients were significantly lower than those of age-matched non-AD control group (P<0.0001), see FIG. 1i. The ROC curve analysis shows that AUC=0.8235, sensitivity=78.43%, specificity=70.91%, see FIG. 1j.

1.6 Comparision of TRPC6 mRNA Levels in the Peripheral Blood Cells between the Following Groups.

a. MCI (Mild cognitive impairment) patients (n=46, mean age=73.1±2.1);

b. age-matched non-MCI control (n=52, mean age=71.1±4.2).

The results show: TRPC6 mRNA levels in the peripheral blood cells of MCI patients were significantly lower than those of age-matched non-MCI control group (***P<0.0001), see FIG. 1k. The ROC curve analysis shows that AUC=0.8370, sensitivity=76.79%, specificity=84.62%, see FIG. 1l.

It can be included that:

TRPC6 mRNA levels in the peripheral blood cells of AD patients were significantly lower than those of age-matched non-AD control group, and did not reduce with aging, and were relevant with dementia index MMSE. Meanwhile, there is no difference in other TRPC members (eg. TRPC5) mRNA levels between AD patients and age-matched non-AD control group. Furthermore, there is no difference in the TRPC6 mRNA levels between PD patients and control group.

Thus, TRPC6 mRNA levels in the peripheral blood cells of AD (including early-stage AD) and MCI patients were significantly lower than those of normal population. It could be used as a specific molecular biomarker in peripheral blood cell for the early prediction and auxillary diagnosis of AD.

EXAMPLE 2

Determination of Relevance between TRPC6 mRNA Level and Aβ in Cell and In Vivo 2.1 Cell Transfection Experiment HEK293 (ATCC CRL-1573) cells were transfected with the Aβ precursor protein APP, and then the HEK293 cells were plated in 12-well plates according to the general methods till the density approached 80%. Each well was transfected with 1ug plasmid using Lipofectamine2000. After 48 hr, the protein expression was detected by immunoblotting, and the protein levels of TRPC6 and TRPC5 were detected under the overexpression of APP.

Figure 2:
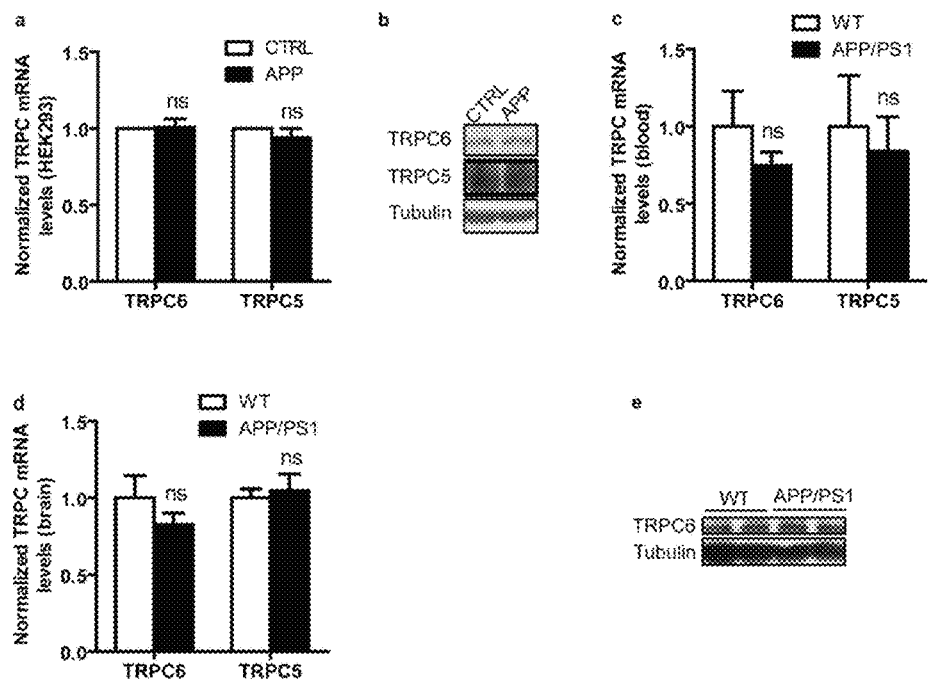
FIG. 2 shows the levels of TRPC6 and TRPC5 in the peripheral blood cells and brain tissues from different type of mice.

The results are shown as FIGS. 2a and b: the overproduction of Aβ in cell models did not affect the mRNA or protein levels of TRPC6 and TRPC5 (mean±SE, n=3); wherein, the actin protein was internal control; ns referred to not significant.

2.2 Animal Experiments

Comparing APP/PS1 mice model to wild-type mice to decide whether the mRNA levels of TRPC6 and TRPC5 change after overproducing Aβ. Total RNA from peripheral blood cells and brains was extracted according to general method 4 from APP/PS1 mice and wild-type mice. After reverse-transcription the mRNA levels of TRPC6 and TRPC5 were detected. The protein levels of TRPC6 were detected using TRPC6 antibody according to general method 5.

FIG. 2c and d show that TRPC6 and TRPC5 mRNA levels in peripheral blood cells and brains of APP/PS1 mice show no significant difference compared to those of WT mice (mean±SE; n=4-10 mice). FIG. 2e shows TRPC6 protein levels in the brains also show no significant difference.

The results of the example show that Aβ accumulation did not result in reduction of the mRNA or protein levels of TRPC6 in cultured cells and mouse model. The lower mRNA level of TRPC6 in peripheral blood of AD patients is unlikely to be a secondary result of Aβ gradual accumulation. Instead, the mRNA level of TRPC6 is lower before disease progression. Thus, TRPC6 is an ideal biomarker for the early diagnosis of AD.

EXAMPLE 3

Determination of the Effect of Expressing TRPCs on Aβ in Cells and In Vivo 3.1 Determining the Effect of TRPCs Overexpression on Aβ Levels in HEK293APP Stable Cells TRPC6 or TRPC5 was overexpressed in HEK293APP stable cell lines respectively (Cells were passaged into 12-well plates till the densities were close to 80%. Each well was transfected with 1 ug plasmid using Lipofectamine 2000, and the Aβ levels in the medium were determined with ELISA after 48 hr).

Figure 3:
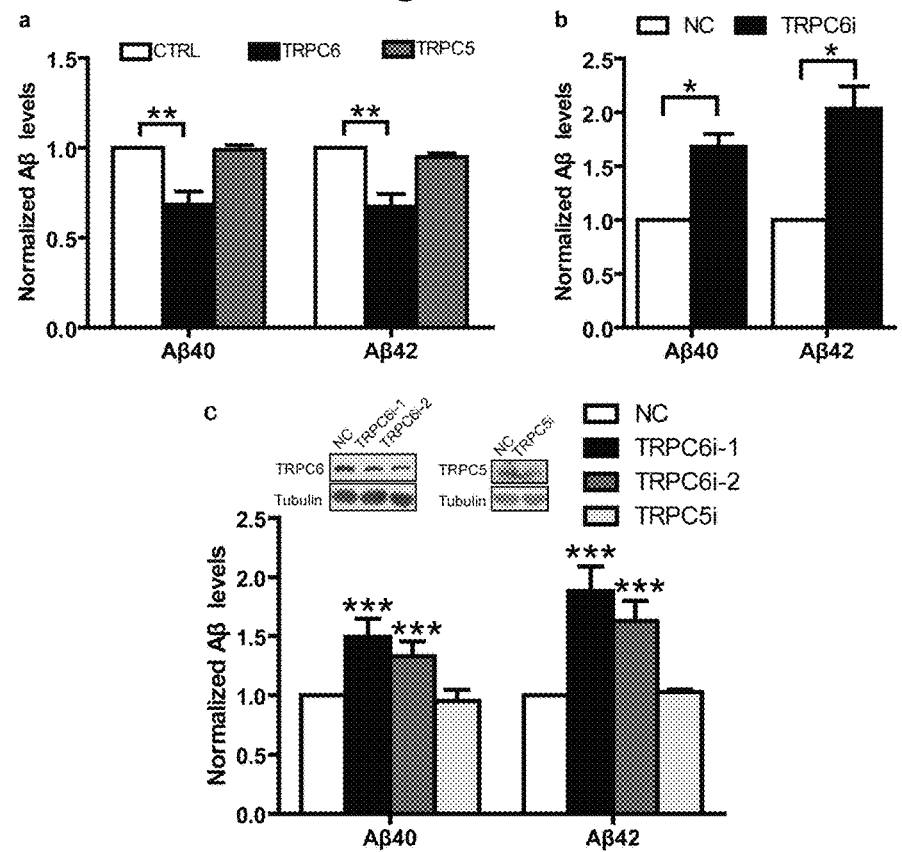
FIG. 3 shows that the expression levels of TRPC6 could affect Aβ levels.

The results were shown in Table 1 and FIG. 3a.

TABLE 1

| HEK293APP Stable cell | Overexpressing Empty Vector | Overexpressing TRPC6 | Overexpressing TRPC5 |
|---|---|---|---|
| Aβ40 | 1 | 0.6839 ± 0.07359 | 0.9900 ± 0.02548 |
| Aβ42 | 1 | 0.6734 ± 0.06994 | 0.9488 ± 0.02053 |

3.2 To Investigate whether Knocking Down TRPC6 or TRPC5 in Primary Cultured Rat Cortical Neurons Could Increase Aβ Levels Fetal rat was collected on the 17th day of SD rat pregnancy. Cortical neurons of the rat brains were separated, obtained, and electrotransfected by Nucleofector Device (Amaxa) with TRPC6 siRNA1 as set forth by SEQ ID NO.:12 (sense strand) and SEQ ID NO.:13 (anti-sense strand), TRPC6 siRNA2 as set forth by SEQ ID NO.:18 (GCUUGACUUUGGAAUGUUATT, sense strand) and SEQ ID NO.:19 (UAACAUUCCAAAGUCAAGCTT, anti-sense strand), control siRNAs as set forth by SEQ ID NO.:14 (sense strand) and SEQ ID NO.:15 (anti-sense strand), and TRPC5 siRNA as set forth by SEQ ID NO.:20 (AACGC-CUUCUCCACGCUCUUU, sense strand) and SEQ ID NO.:21 (AAAGAGCGUGGAGAAGGCGUU, anti-sense strand). 7 days after electrotransfection, Aβ levels in the medium were examined by ELISA.

The results were shown in Table 6 and FIG. 3c.

TABLE 6

| Primary cultured cortical neurons | Control siRNA | TRPC6 siRNA-1 | TRPC6 siRNA-2 | TRPC5 siRNA |
|---|---|---|---|---|
| Aβ40 | 1 | 1.49 ± 0.16 | 1.33 ± 0.13 | 0.96 ± 0.09 |
| Aβ42 | 1 | 1.89 ± 0.21 | 1.63 ± 0.17 | 1.03 ± 0.02 |

Thus, knocking down of TRPC6 increased the Aβ levels in the culture medium, while knocking down of TRPC5 did not affect Aβ levels, see FIG. 3b-c.

3.3 The Effect of Overexpressing TRPC6 in the Neurons of APP/PS1 Mice on Senile Plaques and Aβ Levels TRPC6 transgenic mice overexpressing TRPC6 in the forebrain excitatory neurons were crossed with APP/PS1 mice model. Senile plaques and Aβ levels were examined in APP/PS1 and APP/PS1/TRPC6 offsprings.

The immunostaining of senile plaque: general method 7 (n=11)

Aβ levels: general method 8 (n=13-14)

TBST soluble and insoluble Aβ levels: general method 8 (n=13-14)

Figure 4:
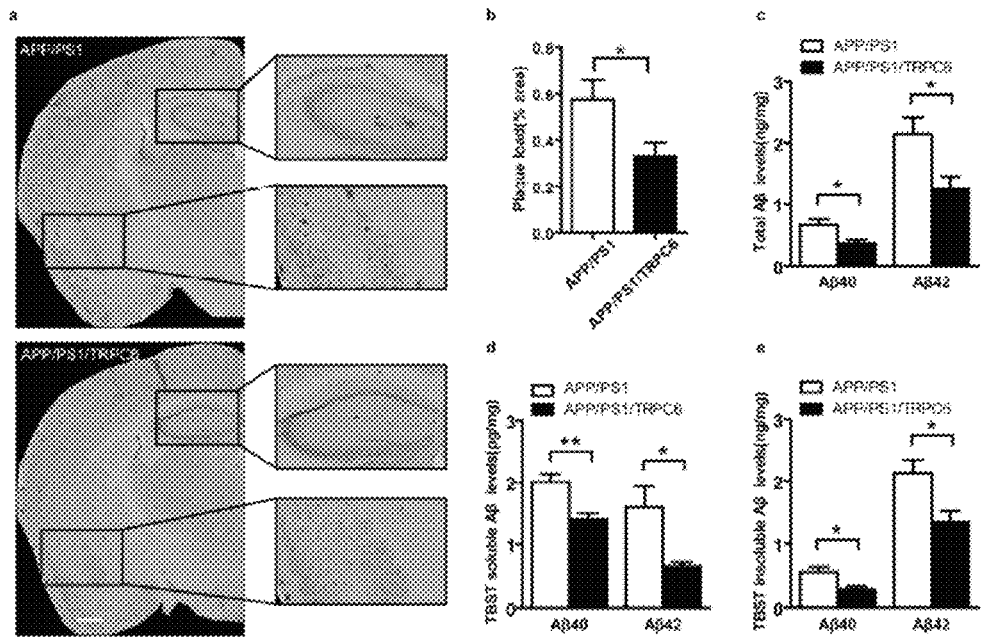
FIG. 4 shows the results and the analysis of senile plaque staining of brain sections from different mice

The results were shown in Table 2 and FIG. 4.

TABLE 2

|  | APP/PS1 mice | APP/PS1/TRPC6mice |
|---|---|---|
| Plaque load | 0.5733 ± 0.08572% | 0.3290 ± 0.06015% |
| Aβ40 levels | 0.6663 ± 0.09649 ng/mg | 0.3635 ± 0.06270 ng/mg |
| Aβ42 levels | 2.143 ± 0.2705 ng/mg | 1.236 ± 0.2159 ng/mg |
| TBST soluble Aβ levels | Aβ40: 2.003 ± 0.1313 pg/mg<br>Aβ42: 1.593 ± 0.3456 pg/mg | Aβ40: 1.398 ± 0.1024 pg/mg<br>Aβ42: 0.6546 ± 0.06741 pg/mg |
| TBST insoluble Aβ levels | Aβ40: 0.5537 ± 0.08580 ng/mg<br>Aβ42: 2.137 ± 0.2149 ng/mg | Aβ40: 0.2958 ± 0.05753 ng/mg<br>Aβ42: 1.361 ± 0.1903 ng/mg |

It could be concluded that TRPC6 could significantly reduce Aβ levels in the cell culture medium. Knocking down of TRPC6 in primary cultured cortical rat neurons significantly increased the Aβ levels in the culture medium; and overexpressing TRPC6 in the neurons could reduce senile plaque and Aβ levels in APP/PS1 mice. Thus, the cell and animal experiments suggested that TRPC6 could reduce Aβ levels.

EXAMPLE 4

Examination of the Effect of TRPC6 on γ-Secretase Cleavage of its Substrates 4.1 The Effect of TRPC6 on γ-Secretase Cleavage of C99, wherein C99 is the C-terminal 99 Residues of APP and is the Direct Substrate of γ-Secretase.

COS7C99 cells overexpressing TRPC6 were obtained by cell-transfection through general method 9 (n=5). The cells were passaged in 12-well plate till the density approached 80%. Each well was transfected with 1 ug plasmid using Lipofectamine 2000, and the Aβ levels in the culture medium were determined with ELISA after 48 h.

Figure 5:
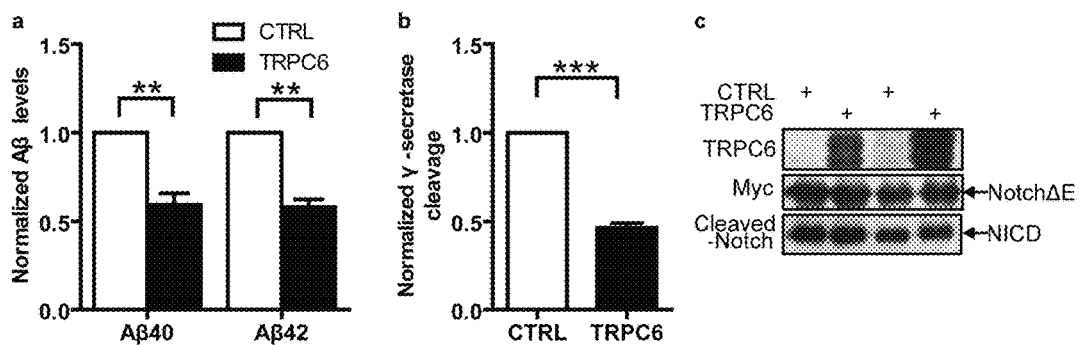
FIG. 5 shows that TRPC6 could specifically inhibit γ-secretase cleavage of APP.

The results were shown in Table 3 and FIG. 5:

TABLE 3

| COS7-C99 stable cells | Aβ40 | Aβ42 | C99-GVP/UAS-Luciferase reporter system |
|---|---|---|---|
| Overexpressing Empty Vector | 1 | 1 | 1 |
| Overexpressing TRPC6 | 0.5949 ± 0.06435 | 0.5805 ± 0.04428 | 0.4650 ± 0.02628 |

As shown in Table 3, overexpressing TRPC6 reduced Aβ produced by C99 cleavage by γ-secretase and decreased the luciferase activity induced by C99 cleavage by γ-secretase.

4.2 The Effect of TRPC6 on γ-Secretase Cleavage of Notch

Cells were passaged in 12-well plate till the density approached 80%. Each well was transfected with 1 ug of TRPC6 and 1 ug of Notch plasmids using Lipofectamine 2000. Immunoblotting was used to examine the expression of Notch protein 48 h later. Wherein, NICD (notch intracellular domain) is the intracellular fragment produced by γ-secretase cleavage of Notch ΔE-myc, reflecting the level of γ-secretase cleavage of Notch.

The results showed that overexpressing TRPC6 did not affect NICD level, which means TRPC6 did not affect γ-secretase cleavage of Notch.

The above results showed that TRPC6 protein (including the wild type of full length protein) specifically inhibited γ-secretase cleavage of APP (C99) to reduce Aβ production, but did not affect γ-secretase cleavage of Notch.

EXAMPLE 5

Screening and Targeting the Transmembrane Polypeptide of TRPC6 Responsible for its Active Effect 5.1 Preliminary Screening of Active Transmembrane Peptide Fragment TRPC6 protein was divided into several peptide fragments. The effect of these fragments on Aβ levels was further screened. The expressing plasmids containing the following TRPC6 fragments were constructed: 1~405aa, 725~930aa, 389~930aa, 389~510aa, 437~633aa, 508~633aa.

Afterwards, HEK293APP stable cells were passaged in 12-well plate till the density approached 80%. Each well was transfected with lug plasmid using Lipofectamine 2000, and the Aβ levels in the culture medium were determined with ELISA after 48 h. The targeting fragment was primarily narrowed down to 437-507aa.

The effect of the major peptide fragments on Aβ levels was shown in Table 4 and FIG. 6.

TABLE 4

| | | Aβ40 | Aβ42 |
|---|---|---|---|
| Empty Vector | | 1 | 1 |
| Variants containing 487-507aa | 389/930aa | 0.7699 ± 0.07728 | 0.7217 ± 0.06950 |
| | 389/510aa | 0.5959 ± 0.08036 | 0.6131 ± 0.1299 |
| | 437/633aa | 0.8146 ± 0.07986 | 0.7096 ± 0.09708 |
| Variants not containing 487-507aa | 508/633aa | 1.016 ± 0.04396 | 1.042 ± 0.02037 |
| | 1/405aa | 0.9674 ± 0.06376 | 0.9822 ± 0.03662 |
| | 725/930aa | 1.007 ± 0.07289 | 0.9822 ± 0.0099 |

The results showed that all the variants containing 437-507aa could reduce Aβ, while variants not containing 437-507aa could not reduce Aβ levels, which indicated that 437-507aa of TRPC6 was crucial for reducing Aβ levels 5.2 Determine the Active Transmembrane Fragment The 437-508aa of TRPC6 contains the the first transmembrane regions(TM1), the first extracellular loop (Loop1), and the second transmembrane regions (TM2). To further narrow down the active domain, we constructed 3 variant plasmids, with TM2 region replacement by TM1 region (C6-mut1), reversal of TM2 sequence (C6-mut2) or point mutations within TM2 region(C6-mut3). Then HEK293APP stable cells were passaged in 12-well plate. When the density was close to 80%, every well was transfected with lug plasmid using Lipofectamine 2000, and the Aβ levels in the medium were determined with ELISA after 48 h. The active fragment was further narrowed down to 487-507aa.

The results were shown in Table 7 and FIGS. 6g and 6h:

TABLE 7

| | Aβ40 | Aβ42 |
|---|---|---|
| Empty Vector | 1 | 1 |
| C6-mut1 | 1.06 ± 0.04 | 1.00 ± 0.01 |
| C6-mut2 | 1.08 ± 0.05 | 1.00 ± 0.01 |
| C6-mut3 | 0.96 ± 0.05 | 0.92 ± 0.06 |

The results showed that all the variant plasmid containing TM2 domain (487-507aa) mutations could not reduce Aβ level, indicating that 487-507aa of TRPC6 was crucial for reducing Aβ levels and was the core area for the inhibition of γ-secretase cleavage of APP.

EXAMPLE 6

The Synthesis of Fusion Peptide Containing 487-507aa and the Detection Thereof 6.1 To Investigate whether the Fusion Peptide Could Reduce Aβ Levels on Cell Level 6.1.1 To Investigate whether the Fusion Peptide Could Reduce Aβ Levels in HEK293APP Stable Cells and Primary Cultured Cortical Neurons In this Example, the second transmembrane domain (487-507aa, TM2) was selected to fuse with cell penetrating peptide TAT and the fusion peptide TAT-TM2 and the mutant thereof TAT-TM2mut were obtained. Their effects on Aβ levels were examined in HEK293APP stable cells. Wherein, the peptides were synthesized by ChinaPeptides, and the sequences were as set forth in Table 12.

The results were shown in Table 8 and Table 9a:

TABLE 8

| | Aβ40 | Aβ42 |
|---|---|---|
| TAT | 1 | 1 |
| TAT-TM2 | 0.39 ± 0.03 | 0.40 ± 0.06 |
| TAT-TM2-mut | 0.89 ± 0.07 | 0.93 ± 0.09 |

TABLE 12

| Fusion Peptides | SEQ ID NO.: | Sequences |
|---|---|---|
| TAT | 16 | GRKKRRQRRRC |
| TAT-TM2 | 17 | TSCFSWMEMLIISWVIGMIWAGRKKRRQRRRC |
| TAT-TM2-mut | 22 | TSCFSWMEMLIISDDIGMDDAGRKKRRQRRRC |
| TAT-TM2-N | 23 | TSCFSWMEMLGRKKRRQRRRC |
| TAT-TM2-C | 24 | IISWVIGMIWAGRKKRRQRRRC |
| TAT-TM2-C-m1 | 25 | DDSWVIGMIWAGRKKRRQRRRC |
| TAT-TM2-C-m2 | 26 | IISDDIGMIWAGRKKRRQRRRC |
| TAT-TM2-C-m3 | 27 | IISWVIGMDDAGRKKRRQRRRC |

6.1.2 The Effect of Different Doses of Fusion Protein TAT-TM2 on Aβ Levels in HEK293APP Stable Cells were Determined.

Figure 9:
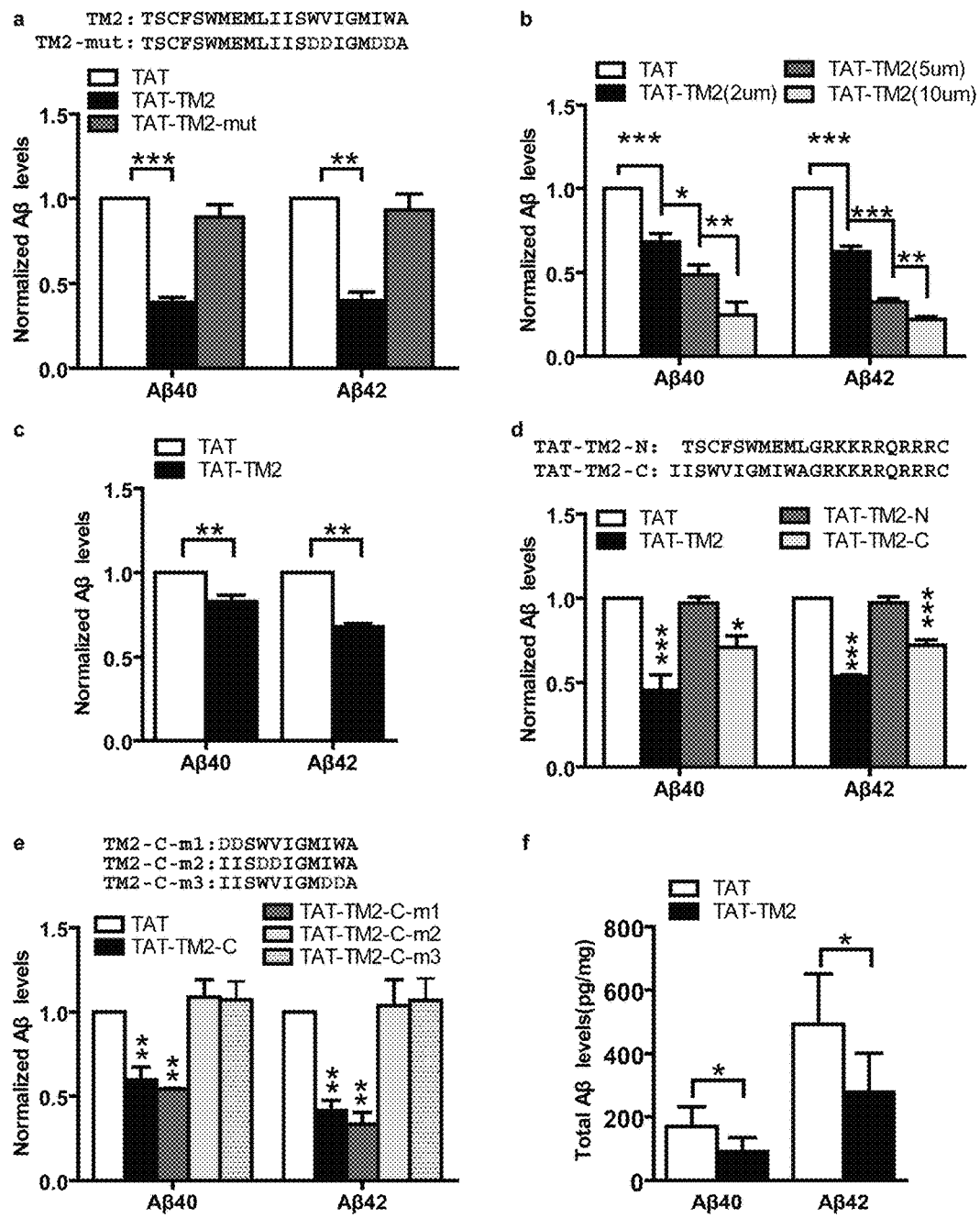
FIG. 9a: the effect of fusion protein TAT-TM2 and the mutated peptide TAT-TM2-mut on Aβ levels in stable transfected HEK293APP cells, wherein, TAT-TM2 could significantly reduce Aβ levels, but TAT-TM2-mut could not significantly affect Aβ levels.
FIG. 9b: ELISA results show that fusion protein TAT-TM2 dose dependently reduces Aβ levels in HEK293APP cells.
FIG. 9c: fusion peptide TAT-TM2 could significantly reduce Aβ levels in primary cultured cortical neurons.
FIG. 9d-e: TAT-TM2-C reduces Aβ levels in HEK293APP cells, but its mutated forms TAT-TM2-C-m2, TAT-TM2-C-m3, or TAT-TM2-N does not affects Aβ levels in HEK293APP cells.
FIG. 9f: fusion peptide TAT-TM2 significantly reduces Aβ levels as well in mice tests in vivo.

The results were shown in Table 5 and FIGS. 6e or 9b.

TABLE 5

|  | Aβ40 | Aβ42 |
| --- | --- | --- |
| TAT | 1 | 1 |
| TAT-TM2 (2 uM) | 0.6825 ± 0.04980 | 0.6244 ± 0.03189 |
| TAT-TM2 (5 uM) | 0.4863 ± 0.05919 | 0.3255 ± 0.02046 |
| TAT-TM2 (10 uM) | 0.2481 ± 0.07630 | 0.2214 ± 0.01597 |

Thus, TAT-TM2 could dose-dependently reduce Aβ levels in HEK293APP cells.

6.1.3 The Effect of the Fusion Peptide TAT-TM2 on Aβ Levels in Primary Cultured Cortical Neurons was Determined and the Results were Shown in FIG. 9c:

Aβ40: 83% of the control group, n=6, p=0.0072;
Aβ42: 68% of the control group, n=3, p=0.0035

Thus, TAT-TM2 could reduce Aβ levels dose-dependently in HEK293APP cells, while TAT-TM2-mut did not affect Aβ levels. TAT-TM2 could also reduce Aβ levels in primary cultured cortical neurons.

6.1.4 The Effect of TAT-TM2 Variants on Aβ Levels in HEK293APP Cells was Determined.

To search for shorter fragments which could inhibit Aβ levels, TM2 was divided into N- and C-terminals and fused with TAT respectively. The effects of TAT-TM2-N, TAT-TM2-C and TAT-TM2-C mutant on Aβ levels in HEK293APP cells was examined. The peptide fragments were synthesized by ChinaPeptides, and the sequences were as set forth in FIG. 12. The results were shown in Table 9 and FIGS. 9d-e:

TABLE 9

|  | Aβ40 | Aβ42 |
| --- | --- | --- |
| TAT | 1 | 1 |
| TAT-TM2-N | 0.97 ± 0.04 | 0.97 ± 0.04 |
| TAT-TM2-C | 0.71 ± 0.07 | 0.72 ± 0.03 |
| TAT-TM2-C-m1 | 0.54 ± 0.01 | 0.33 ± 0.07 |
| TAT-TM2-C-m2 | 1.09 ± 0.10 | 1.04 ± 0.15 |
| TAT-TM2-C-m3 | 1.07 ± 0.11 | 1.07 ± 0.13 |

The results showed that TAT-TM2-C could reduce Aβ levels in HEK293APP cells, while its mutational variants TAT-TM2-C-m2 and TAT-TM2-C-m3 as well as TAT-TM2-N could not affect Aβ levels. TM2-C was essential for TM2 to down-regulate the Aβ levels.

6.2 To Investigate whether TAT-TM2 Could Reduce Aβ Level in APP/PS1 Mice

TAT or TAT-TM2 was intraperitoneally injected into APP/PS1 mice, and brain tissue samples were prepared 3 hours later and the Aβ levels were determined: general method 8 (n=8)

The results were shown in Table 10 and FIG. 9f.

TABLE 10

|  | Aβ40 (pg/mg) | Aβ42 (pg/mg) |
| --- | --- | --- |
| TAT | 169.70 ± 61.78 | 492.60 ± 157.70 |
| TAT-TM2 | 91.12 ± 43.56 | 277.40 ± 124.10 |

Thus, TAT-TM2 could reduce Aβ levels in APP/PS1 mice as well.

EXAMPLE 7

Compound Screening

In the present example, the medications were screened on mRNA levels according to the following method:

In the test groups, a testing compound was added into the culture medium of HEK293 cells, and TRPC6 mRNA expression was observed in the cells of the test group (total RNA was extracted and reverse transcribed to cDNA, and the expression level was determined by fluorescent quantitation real-time PCR); in the control group, no compound was added into the same culture medium of the cells, and TRPC6 expression levels in said cells were observed in the control group;

If the TRPC6 mRNA levels in the test group were higher than that in the control group, it can be concluded that said compound was a candidate compound for prevention or treatment of AD by improving the expression of TRPC6.

Results:

5 compounds were tested double-blindedly. The results indicated that the compound C could upregulate TRPC6 expression. A further analysis indicated that said compound C turned out to be $CoCl_2$

EXAMPLE 8

Determination of the Correlation between APOE Genotype and TRPC6 mRNA Levels 8.1 Correlation between APOE Genotype and TRPC6 mRNA Levels in Peripheral Blood Cells Sporadic AD, age-matched non-AD control, young non-AD control and all subjects were subgrouped according their APOE genotypes. Intergroup analysis was then conducted.

Figure 8:
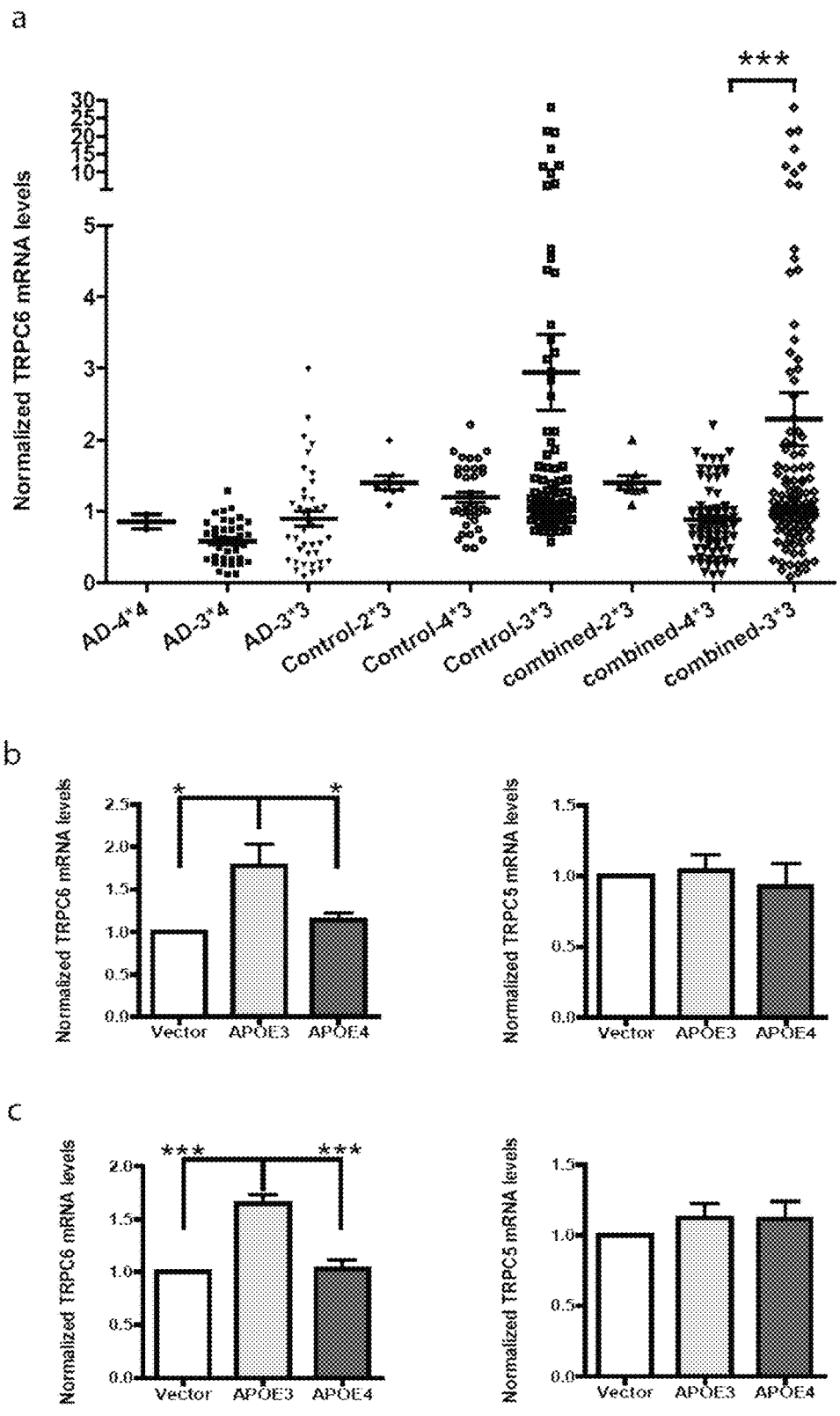
FIG. 8a: APOE3 carriers have higher TRPC6 mRNA levels while APOE4 carriers have lower TRPC6 mRNA levels (***P<0. 001); wherein, AD-4*4, AD-3*3 and AD-3*4 represent AD patients who are APOE4 homozygotes, APOE3 homozygotes, and APOE3 and 4 heterozygotes, respectively. Control-2*3, Control-3*3 and Control-3*4 represent control individuals who are APOE2 and 3 heterozygotes, APOE3 homozygotes and APOE3 and 4 heterozygotes, respectively. Combined-2*3, Combined-3*3 and Combined-3*4 represent all individuals who are APOE2 and 3 heterozygotes, APOE3 homozygotes and APOE3 and 4 heterozygotes, respectively.
FIG. 8b: the culture supernatant containing APOE3 could increase TRPC6 mRNA levels in Jurkat cells, but the culture supernatant containing APOE4 could not affect TRPC6 mRNA levels in Jurkat cells.
FIG. 8c: the culture supernatant containing APOE3 could increase TRPC6 mRNA levels in rat neurons, but the culture supernatant containing APOE4 could not affect TRPC6 mRNA levels in rat neurons.

The results showed that TRPC6 mRNA levels of APOE3 carriers were higher and TRPC6 mRNA levels of APOE4 carriers were lower (***P<0.001), see FIG. 8a. Wherein, AD-4*4, AD-3*3 and AD-3*4 respectively represents AD patients with APOE4 homozygotes, APOE3 homozygotes and APOE3 and 4 heterozygotes. Control-2*3, Control-3*3 and Control-3*4 respectively represents controls with APOE2 and 3 heterozygotes, APOE3 homozygotes and APOE3 and 4 heterozygotes. Combined-2*3, Combined-3*3 and Combined-3*4 respectively represents all the subjects with APOE2 and 3 heterozygotes, APOE3 homozygotes and APOE3 and 4 heterozygotes.

Conclusion: it could be seen from AD and control groups that the APOE3*3 carriers have higher TRPC6 mRNA mean levels than APOE3*4 carriers. After all the individuals were divided in groups according to the APOE genotypes, the TRPC6 mRNA level of APOE3*3 carriers was significantly higher than TRPC6 mRNA levels in APOE3*4 carriers (P<0.001).

8.2 Cell Experiments

The culture medium containing different APOE isoforms were added into the Jurkat cells (human T cell line from peripheral blood). The mRNA levels of TRPC6 and TRPC5 were detected after 5 hr (mean±SE, n=5).

The results showed that the culture medium supernatant containing APOE3 could increase TRPC6 mRNA levels in Jurkat cells, but the culture medium supernatant containing APOE4 could not affect TRPC6 mRNA levels in Jurkat cells. The culture medium supernatant containing APOE3 or APOE4 could not affect TRPC5 mRNA levels in Jurkat cells, see FIG. 8b.

The culture medium supernatant containing different APOE isoforms were added into rat neurons cultured in vitro for 8 days. The mRNA levels of TRPC6 and TRPC5 were detected after 2 hr (mean±SE, n=8).

The results showed that the cultured medium supernatant containing APOE3 could increase the TRPC6 mRNA levels in rat neurons, but the cultured medium supernatant containing APOE4 could not affect the TRPC6 mRNA levels in rat neurons. The cultured medium supernatant containing APOE3 or APOE4 could not affect the TRPC5 mRNA levels in rat neurons, see FIG. 8c.

EXAMPLE 9

To Determine the Effect of TAT-TM2 on the γ-Secretase Cleavage of the Substrate Thereof 9.1 The Effect of TAT-TM2 on γ-Secretase Cleavage of C99

C99 is the C-terminal 99 amino acids of APP and the direct substrate of γ-secretase. C0S7C99 cells were passaged in 12-well plate till the density approached 100%. Each well was treated with 5 um peptide for 12 h and the Aβ levels in the culture medium was determined with ELISA.

Figure 10:
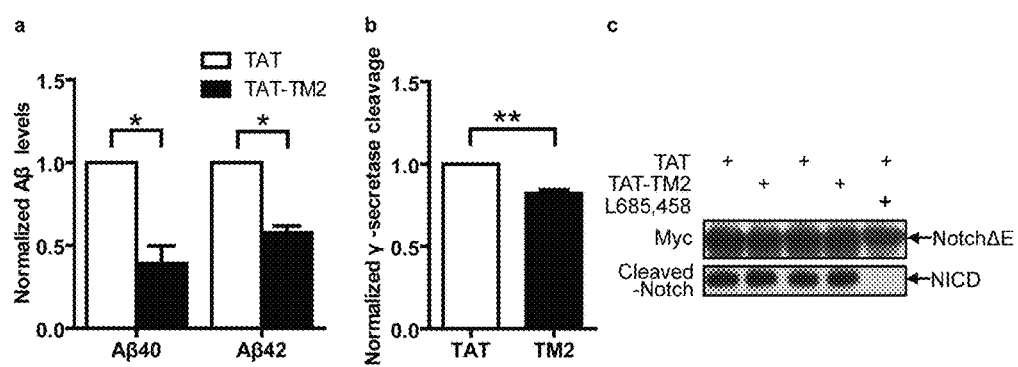
FIG. 10a-b: TAT-TM2 reduces Aβ produced by γ-secretase cleavage of C99 and luciferase activity induced by γ-secretase cleavage of C99.
FIG. 10c: TAT-TM2 does not affect NICD levels, suggesting TAT-TM2 does not affect γ-secretase cleavage of Notch.

The results were shown in Table 11 and FIG. 10.

TABLE 11

| C0S7-C99 stable cells | Aβ40 | Aβ42 | C99-GVP/UAS luciferase reporter system |
|---|---|---|---|
| TAT | 1 | 1 | 1 |
| TAT-TM2 | 0.39 ± 0.11 | 0.58 ± 0.04 | 0.82 ± 0.02 |

As shown in Table 11, TAT-TM2 reduced Aβ produced by γ-secretase cleavage of C99 and decreased the luciferase activity induced by C99 cleavage by γ-secretase.

9.2 The Effect of TAT-TM2 on γ-Secretase Cleavage of Notch

Cells were passaged in 12-well plate till the density approached 80%, Each well was transfected with 1 ug Notch plasmid using Lipofectamine 2000. 24 hr later, cells were treated with 5 um peptide for 12 hr. The Notch protein expression was determined by immunoblotting. Wherein, NICD (notch intracellular domain) was the intracellular fragment produced by γ-secretase cleavage of NotchΔE-myc, reflecting the level of γ-secretase cleavage of Notch.

The results were shown in FIGS. 6f or 10c. TAT-TM2 did not affect NICD level, which means TAT-TM2 did not affect γ-secretase cleavage of Notch.

The above results showed that TAT-TM2 specifically inhibit γ-secretase cleavage of APP (C99) so as to reduce Aβ production, but not affect γ-secretase cleavage of Notch.

All references mentioned in the present invention are incorporated herein by reference, as each of them is individually cited herein by reference. Further, it should be understood that, after reading the above contents, the skilled person can make various modifications or changes to the present invention. All these equivalents also fall into the scope defined by the appending claims of the present application.

The invention claimed is:

1. A detection method for early auxiliary diagnosis of Alzheimer's disease (AD), comprising:
    (a) extracting mRNAs in peripheral blood or peripheral blood cells obtained from a subject, which is a mammal;
    (b) generating cDNAs from the mRNAs obtained in (a);
    (c) measuring the level of nucleic acids encoding TRPC6 in the cDNAs obtained in (b) by performing an amplification assay which comprises contacting the cDNAs with a pair of primers consisting of SEQ ID NO: 1 and SEQ ID NO: 2; and
    (d) determining whether the subject is at risk for AD, wherein an elevated level of TRPC6 measured by step (c) as relative to the level of TRPC6 in a non-AD control population suggests a higher AD risk or susceptibility of said subject than the non-AD control population.

2. The method according to claim 1, wherein said amplification assay is a real-time fluorescence quantitative polymerase chain reaction (PCR) assay.

3. The method according to claim 1, wherein said subject is a human.

4. The method according to claim 1, wherein said amplification assay is conducted using a kit, which comprises the pair of primers.

* * * * *

SEQUENCE LISTING

```
<160> NUMBER OF SEQ ID NOS: 27

<210> SEQ ID NO 1
<211> LENGTH: 20
<212> TYPE: DNA
<213> ORGANISM: artificial sequence
<220> FEATURE:
<223> OTHER INFORMATION: primer

<400> SEQUENCE: 1
ccaggaaatt gaggatgacg                                               20

<210> SEQ ID NO 2
<211> LENGTH: 20
<212> TYPE: DNA
<213> ORGANISM: artificial sequence
<220> FEATURE:
<223> OTHER INFORMATION: primer

<400> SEQUENCE: 2
tgccctcctc aaagtaggaa                                               20

<210> SEQ ID NO 3
<211> LENGTH: 2793
<212> TYPE: DNA
<213> ORGANISM: Mus musculus
<220> FEATURE:
<221> NAME/KEY: CDS
<222> LOCATION: (1459)..(1521)
```

<400> SEQUENCE: 3

```
atgagccaga gcccgaggtt cgtgacccgg aggggcggct ctctaaaggc tgcccctgga      60
gccggcaccc ggcgcaacga gagccaggac tatttgctga tggacgagct gggagacgac     120
ggctaccogc agctcccgct gccaccgtat ggctactacc ccagcttccg gggtaatgaa     180
aacagactga ctcaccggcg gcagacgatt cttcgtgaga agggaagaag gttagctaat     240
cgaggaccag catacatgtt taatgatcat caacaagcc tgtctattga ggaagaacgc      300
tttctagatg cagctgaata tggcaacatc ccagtggtgc ggaagatgct agaagagtgt     360
cattccctca atgttaactg tgtggattac atgggccaga atgccctaca gctggctgtg     420
gccaatgagc acttggaaat cacagagctg ctactcaaga aggaaaactt gtctcgagtt     480
ggggatgctt acttttagc cattagtaaa ggttatgtac ggattgtgga ggcaatcctc      540
aaccatccag cttttgctga aggcaaaagg ttagcgacaa gccccagcca gtctgaactt     600
cagcaagatg acttttatgc ctatgatgaa gatgggacgc ggttctccca tgatgtgacc     660
ccaatcattc tcgctgcaca ttgccaggaa tatgaaattg tgcataccct cctgagaaag     720
ggtgcccgga ttgagcggcc tcatgattac ttctgcaagt gtacagaatg cagccagaag     780
cagaagcatg attccttcag ccactctaga tccaggatca atgcatacaa aggtctggca     840
agtccagcat acctgtcatt gtccagtgaa gatccagtca tgactgcttt agaacttagc     900
aatgagctgg cagtgcttgc caacattgag aaagagttca gaatgactca caggaagctg     960
tctatgcagt gcaaggattt cgttgttggt ctcttggacc tctgcagaaa cacagaggaa    1020
gtggaggcca tcctgaatgg ggatgcagag actcgccagc ccggggactt cggccgtcca    1080
aatctcagcc gtttaaaact tgctattaag tatgaagtaa aaaaatttgt ggctcatcca    1140
aactgtcagc aacagctcct gtccatatgg tatgagaacc tctctggttt acggcagcag    1200
accatggcag tgaagttcct cgtggtcctt gctgttgcca ttggattgcc cttcctggct    1260
ctcatatact ggtgtgctcc ttgcagcaag atggggaaga tattgcgagg accgttcatg    1320
aagtttgtag cacacgcagc ctccttcacc attttcctgg ggctgctcgt catgaatgca    1380
gctgacagat ttgaaggcac caagctcctc cctaatgaaa ccagcacaga taatgcaagg    1440
cagctgttca ggatgaaa aca tcc tgt ttc tca tgg atg gag atg ctc att    1491
                       Thr Ser Cys Phe Ser Trp Met Glu Met Leu Ile
                        1               5                       10
ata tcc tgg gta ata ggc atg ata tgg gct gaatgtaaag aaatctggac        1541
Ile Ser Trp Val Ile Gly Met Ile Trp Ala
             15                  20
tcaaggcccc aaagaatact tatttgagtt gtggaatatg cttgactttg aatgctggc    1601
aatctttgca gcatcattca ttgcaagatt tatggcgttc tggcatgcat ccaaagctca    1661
gagcatcatt gatgcaaatg atactttaaa ggatttgaca aaagtcacac tgggggacaa    1721
cgttaaatac tacaatctgg ccaggataaa gtgggaccct actgatcctc agatcatctc    1781
tgaaggtctt tatgcaatcg ctgtggtttt aagtttctcc agaatagctt acattttacc    1841
agcaaatgaa agctttggac ctctgcagat tcacttggga agaacagtga agatatctt     1901
caaattcatg gtcatattca tcatggtgtt tgtagccttt atgattggaa tgttcaacct    1961
ttactcctac tacattggcg caaaacagaa tgaagcattc acaacagttg aggaaagttt    2021
taagacactg ttctgggcta tctttggtct tctgaagtg aagtcagtgg tcattaacta     2081
caatcacaag ttcattgaaa acatcggcta cgttctgtat ggtgtctata atgtcacaat    2141
```

-continued

```
ggtcattgtt ttgctaaata tgttaattgc gatgatcaat agttcattcc aggaaattga    2201
ggatgatgcg gacgtggagt ggaagtttgc aagggccaaa ttgtggtttt cctactttga    2261
ggagggagag acacttcctg tccccttcaa tcttgtacca agtccaaaat ccttgcttta    2321
tctcctattg aaatttaaga aatggatgtg tgagctcatc cagggtcaaa agcaaggctt    2381
ccaagaagat gcagagatga acaagagaaa tgaagaaaag aaatttggaa tttcaggaag    2441
tcacgaagac ctttcaaaat tttcacttga caaaaatcag ttggcacaca acaaacaatc    2501
aagtacaagg agctcagaag attatcattt aaatagtttc agtaaccctc aagacaata    2561 tcagaaaatc atgaagagac tcattaaaag atatgtattg caggcccaga ttgataagga    2621
gagcgatgag gtgaatgaag gggaattgaa ggaaattaag caagacatct caagtctccg    2681
ttatgaactc cttgaagaga aatcacagaa cacagaagac ctagcagagc tcattagaaa    2741
actcggggag agactgtcgt tagagccaaa gctggaggaa agccgcagat ag            2793
```

<210> SEQ ID NO 4
<211> LENGTH: 21
<212> TYPE: PRT
<213> ORGANISM: Mus musculus

<400> SEQUENCE: 4

Thr Ser Cys Phe Ser Trp Met Glu Met Leu Ile Ile Ser Trp Val Ile
1               5                   10                  15

Gly Met Ile Trp Ala
            20

<210> SEQ ID NO 5
<211> LENGTH: 930
<212> TYPE: PRT
<213> ORGANISM: Mus musculus

<400> SEQUENCE: 5

Met Ser Gln Ser Pro Arg Phe Val Thr Arg Arg Gly Gly Ser Leu Lys
1               5                   10                  15

Ala Ala Pro Gly Ala Gly Thr Arg Arg Asn Glu Ser Gln Asp Tyr Leu
            20                  25                  30

Leu Met Asp Glu Leu Gly Asp Asp Gly Tyr Pro Gln Leu Pro Leu Pro
        35                  40                  45

Pro Tyr Gly Tyr Pro Ser Phe Arg Gly Asn Glu Asn Arg Leu Thr
    50                  55                  60

His Arg Arg Gln Thr Ile Leu Arg Glu Lys Gly Arg Arg Leu Ala Asn
65                  70                  75                  80

Arg Gly Pro Ala Tyr Met Phe Asn Asp His Ser Thr Ser Leu Ser Ile
                85                  90                  95

Glu Glu Glu Arg Phe Leu Asp Ala Ala Glu Tyr Gly Asn Ile Pro Val
            100                 105                 110

Val Arg Lys Met Leu Glu Glu Cys His Ser Leu Asn Val Asn Cys Val
        115                 120                 125

Asp Tyr Met Gly Gln Asn Ala Leu Gln Leu Ala Val Ala Asn Glu His
    130                 135                 140

Leu Glu Ile Thr Glu Leu Leu Leu Lys Lys Glu Asn Leu Ser Arg Val
145                 150                 155                 160

Gly Asp Ala Leu Leu Leu Ala Ile Ser Lys Gly Tyr Val Arg Ile Val
                165                 170                 175

Glu Ala Ile Leu Asn His Pro Ala Phe Ala Glu Gly Lys Arg Leu Ala
            180                 185                 190

```
Thr Ser Pro Ser Gln Ser Glu Leu Gln Gln Asp Asp Phe Tyr Ala Tyr
            195                 200                 205
Asp Glu Asp Gly Thr Arg Phe Ser His Asp Val Thr Pro Ile Ile Leu
    210                 215                 220
Ala Ala His Cys Gln Glu Tyr Glu Ile Val His Thr Leu Leu Arg Lys
225                 230                 235                 240
Gly Ala Arg Ile Glu Arg Pro His Asp Tyr Phe Cys Lys Cys Thr Glu
                245                 250                 255
Cys Ser Gln Lys Gln Lys His Asp Ser Phe Ser His Ser Arg Ser Arg
            260                 265                 270
Ile Asn Ala Tyr Lys Gly Leu Ala Ser Pro Ala Tyr Leu Ser Leu Ser
            275                 280                 285
Ser Glu Asp Pro Val Met Thr Ala Leu Glu Leu Ser Asn Glu Leu Ala
    290                 295                 300
Val Leu Ala Asn Ile Glu Lys Glu Phe Lys Asn Asp Tyr Arg Lys Leu
305                 310                 315                 320
Ser Met Gln Cys Lys Asp Phe Val Val Gly Leu Leu Asp Leu Cys Arg
                325                 330                 335
Asn Thr Glu Glu Val Glu Ala Ile Leu Asn Gly Asp Ala Glu Thr Arg
            340                 345                 350
Gln Pro Gly Asp Phe Gly Arg Pro Asn Leu Ser Arg Leu Lys Leu Ala
    355                 360                 365
Ile Lys Tyr Glu Val Lys Lys Phe Val Ala His Pro Asn Cys Gln Gln
370                 375                 380
Gln Leu Leu Ser Ile Trp Tyr Glu Asn Leu Ser Gly Leu Arg Gln Gln
385                 390                 395                 400
Thr Met Ala Val Lys Phe Leu Val Val Leu Ala Val Ala Ile Gly Leu
                405                 410                 415
Pro Phe Leu Ala Leu Ile Tyr Trp Cys Ala Pro Cys Ser Lys Met Gly
            420                 425                 430
Lys Ile Leu Arg Gly Pro Phe Met Lys Phe Val Ala His Ala Ala Ser
            435                 440                 445
Phe Thr Ile Phe Leu Gly Leu Leu Val Met Asn Ala Ala Asp Arg Phe
    450                 455                 460
Glu Gly Thr Lys Leu Leu Pro Asn Glu Thr Ser Thr Asp Asn Ala Arg
465                 470                 475                 480
Gln Leu Phe Arg Met Lys Thr Ser Cys Phe Ser Trp Met Glu Met Leu
                485                 490                 495
Ile Ile Ser Trp Val Ile Gly Met Ile Trp Ala Glu Cys Lys Glu Ile
            500                 505                 510
Trp Thr Gln Gly Pro Lys Glu Tyr Leu Phe Glu Leu Trp Asn Met Leu
            515                 520                 525
Asp Phe Gly Met Leu Ala Ile Phe Ala Ala Ser Phe Ile Ala Arg Phe
    530                 535                 540
Met Ala Phe Trp His Ala Ser Lys Ala Gln Ser Ile Ile Asp Ala Asn
545                 550                 555                 560
Asp Thr Leu Lys Asp Leu Thr Lys Val Thr Leu Gly Asp Asn Val Lys
                565                 570                 575
Tyr Tyr Asn Leu Ala Arg Ile Lys Trp Asp Pro Thr Asp Pro Gln Ile
            580                 585                 590
Ile Ser Glu Gly Leu Tyr Ala Ile Ala Val Val Leu Ser Phe Ser Arg
            595                 600                 605
```

-continued

```
Ile Ala Tyr Ile Leu Pro Ala Asn Glu Ser Phe Gly Pro Leu Gln Ile
        610                 615                 620

Ser Leu Gly Arg Thr Val Lys Asp Ile Phe Lys Phe Met Val Ile Phe
625                 630                 635                 640

Ile Met Val Phe Val Ala Phe Met Ile Gly Met Phe Asn Leu Tyr Ser
                645                 650                 655

Tyr Tyr Ile Gly Ala Lys Gln Asn Glu Ala Phe Thr Thr Val Glu Glu
                660                 665                 670

Ser Phe Lys Thr Leu Phe Trp Ala Ile Phe Gly Leu Ser Glu Val Lys
        675                 680                 685

Ser Val Val Ile Asn Tyr Asn His Lys Phe Ile Glu Asn Ile Gly Tyr
        690                 695                 700

Val Leu Tyr Gly Val Tyr Asn Val Thr Met Val Ile Val Leu Leu Asn
705                 710                 715                 720

Met Leu Ile Ala Met Ile Asn Ser Ser Phe Gln Ile Glu Asp Asp
                725                 730                 735

Ala Asp Val Glu Trp Lys Phe Ala Arg Ala Lys Leu Trp Phe Ser Tyr
                740                 745                 750

Phe Glu Glu Gly Arg Thr Leu Pro Val Pro Phe Asn Leu Val Pro Ser
        755                 760                 765

Pro Lys Ser Leu Leu Tyr Leu Leu Lys Phe Lys Lys Trp Met Cys
770                 775                 780

Glu Leu Ile Gln Gly Gln Lys Gln Gly Phe Gln Asp Ala Glu Met
785                 790                 795                 800

Asn Lys Arg Asn Glu Glu Lys Lys Phe Gly Ile Ser Gly Ser His Glu
                805                 810                 815

Asp Leu Ser Lys Phe Ser Leu Asp Lys Asn Gln Leu Ala His Asn Lys
        820                 825                 830

Gln Ser Ser Thr Arg Ser Ser Glu Asp Tyr His Leu Asn Ser Phe Ser
        835                 840                 845

Asn Pro Pro Arg Gln Tyr Gln Lys Ile Met Lys Arg Leu Ile Lys Arg
        850                 855                 860

Tyr Val Leu Gln Ala Gln Ile Asp Lys Glu Ser Asp Glu Val Asn Glu
865                 870                 875                 880

Gly Glu Leu Lys Glu Ile Lys Gln Asp Ile Ser Ser Leu Arg Tyr Glu
                885                 890                 895

Leu Leu Glu Glu Lys Ser Gln Asn Thr Glu Asp Leu Ala Glu Leu Ile
                900                 905                 910

Arg Lys Leu Gly Glu Arg Leu Ser Leu Glu Pro Lys Leu Glu Glu Ser
        915                 920                 925

Arg Arg
    930
```

<210> SEQ ID NO 6
<211> LENGTH: 20
<212> TYPE: DNA
<213> ORGANISM: artificial sequence
<220> FEATURE:
<223> OTHER INFORMATION: primer

<400> SEQUENCE: 6
gcaaggaagt ggtgggcgct                                               20

<210> SEQ ID NO 7
<211> LENGTH: 22
<212> TYPE: DNA

```
<213> ORGANISM: artificial sequence
<220> FEATURE:
<223> OTHER INFORMATION: primer

<400> SEQUENCE: 7
agtggggacc tgcttctctc cg                                              22

<210> SEQ ID NO 8
<211> LENGTH: 20
<212> TYPE: DNA
<213> ORGANISM: artificial sequence
<220> FEATURE:
<223> OTHER INFORMATION: primer

<400> SEQUENCE: 8
ggctacagct tcaccaccac                                                 20

<210> SEQ ID NO 9
<211> LENGTH: 20
<212> TYPE: DNA
<213> ORGANISM: artificial sequence
<220> FEATURE:
<223> OTHER INFORMATION: primer

<400> SEQUENCE: 9
gagtacttgc gctcaggagg                                                 20

<210> SEQ ID NO 10
<211> LENGTH: 20
<212> TYPE: DNA
<213> ORGANISM: artificial sequence
<220> FEATURE:
<223> OTHER INFORMATION: primer

<400> SEQUENCE: 10
gttctccgtt tgcactcagg                                                 20

<210> SEQ ID NO 11
<211> LENGTH: 20
<212> TYPE: DNA
<213> ORGANISM: artificial sequence
<220> FEATURE:
<223> OTHER INFORMATION: primer

<400> SEQUENCE: 11
gctggggtag tagccatacg                                                 20

<210> SEQ ID NO 12
<211> LENGTH: 21
<212> TYPE: DNA
<213> ORGANISM: artificial sequence
<220> FEATURE:
<223> OTHER INFORMATION: RNAi

<400> SEQUENCE: 12
cgguggucau caacuacaat t                                               21

<210> SEQ ID NO 13
<211> LENGTH: 21
<212> TYPE: DNA
<213> ORGANISM: artificial sequence
<220> FEATURE:
<223> OTHER INFORMATION: RNAi

<400> SEQUENCE: 13
uuguaguuga ugaccaccgt t                                               21
```

```
<210> SEQ ID NO 14
<211> LENGTH: 21
<212> TYPE: DNA
<213> ORGANISM: artificial sequence
<220> FEATURE:
<223> OTHER INFORMATION: RNAi

<400> SEQUENCE: 14
gcacaccgaa ggauauucut t                                              21

<210> SEQ ID NO 15
<211> LENGTH: 21
<212> TYPE: DNA
<213> ORGANISM: artificial sequence
<220> FEATURE:
<223> OTHER INFORMATION: RNAi

<400> SEQUENCE: 15
agaauauccu ucggugugct t                                              21

<210> SEQ ID NO 16
<211> LENGTH: 11
<212> TYPE: PRT
<213> ORGANISM: artificial sequence
<220> FEATURE:
<223> OTHER INFORMATION: fusion peptide

<400> SEQUENCE: 16

Gly Arg Lys Lys Arg Arg Gln Arg Arg Arg Cys
1               5                   10

<210> SEQ ID NO 17
<211> LENGTH: 32
<212> TYPE: PRT
<213> ORGANISM: artificial sequence
<220> FEATURE:
<223> OTHER INFORMATION: fusion peptide

<400> SEQUENCE: 17

Thr Ser Cys Phe Ser Trp Met Glu Met Leu Ile Ile Ser Trp Val Ile
1               5                   10                  15

Gly Met Ile Trp Ala Gly Arg Lys Lys Arg Arg Gln Arg Arg Arg Cys
            20                  25                  30

<210> SEQ ID NO 18
<211> LENGTH: 21
<212> TYPE: DNA
<213> ORGANISM: artificial sequence
<220> FEATURE:
<223> OTHER INFORMATION: siRNA

<400> SEQUENCE: 18
gcuugacuuu ggaauguuat t                                              21

<210> SEQ ID NO 19
<211> LENGTH: 21
<212> TYPE: DNA
<213> ORGANISM: artificial sequence
<220> FEATURE:
<223> OTHER INFORMATION: siRNA

<400> SEQUENCE: 19
uaacauucca aagucaagct t                                              21
```

```
<210> SEQ ID NO 20
<211> LENGTH: 21
<212> TYPE: RNA
<213> ORGANISM: artificial sequence
<220> FEATURE:
<223> OTHER INFORMATION: siRNA

<400> SEQUENCE: 20
aacgccuucu ccacgcucuu u                                              21

<210> SEQ ID NO 21
<211> LENGTH: 21
<212> TYPE: RNA
<213> ORGANISM: artificial sequence
<220> FEATURE:
<223> OTHER INFORMATION: siRNA

<400> SEQUENCE: 21
aaagagcgug gagaaggcgu u                                              21

<210> SEQ ID NO 22
<211> LENGTH: 32
<212> TYPE: PRT
<213> ORGANISM: artificial sequence
<220> FEATURE:
<223> OTHER INFORMATION: fusion protein

<400> SEQUENCE: 22

Thr Ser Cys Phe Ser Trp Met Glu Met Leu Ile Ile Ser Asp Asp Ile
1               5                   10                  15
Gly Met Asp Asp Ala Gly Arg Lys Lys Arg Gln Arg Arg Cys
            20                  25                  30

<210> SEQ ID NO 23
<211> LENGTH: 21
<212> TYPE: PRT
<213> ORGANISM: artificial sequence
<220> FEATURE:
<223> OTHER INFORMATION: fusion protein

<400> SEQUENCE: 23

Thr Ser Cys Phe Ser Trp Met Glu Met Leu Gly Arg Lys Lys Arg Arg
1               5                   10                  15
Gln Arg Arg Arg Cys
            20

<210> SEQ ID NO 24
<211> LENGTH: 22
<212> TYPE: PRT
<213> ORGANISM: artificial sequence
<220> FEATURE:
<223> OTHER INFORMATION: fusion protein

<400> SEQUENCE: 24

Ile Ile Ser Trp Val Ile Gly Met Ile Trp Ala Gly Arg Lys Lys Arg
1               5                   10                  15
Arg Gln Arg Arg Arg Cys
            20

<210> SEQ ID NO 25
<211> LENGTH: 22
<212> TYPE: PRT
<213> ORGANISM: artificial sequence
<220> FEATURE:
<223> OTHER INFORMATION: fusion protein
```

```
<400> SEQUENCE: 25

Asp Asp Ser Trp Val Ile Gly Met Ile Trp Ala Gly Arg Lys Lys Arg
1               5                   10                  15

Arg Gln Arg Arg Arg Cys
            20

<210> SEQ ID NO 26
<211> LENGTH: 22
<212> TYPE: PRT
<213> ORGANISM: artificial sequence
<220> FEATURE:
<223> OTHER INFORMATION: fusion protein

<400> SEQUENCE: 26

Ile Ile Ser Asp Asp Ile Gly Met Ile Trp Ala Gly Arg Lys Lys Arg
1               5                   10                  15

Arg Gln Arg Arg Arg Cys
            20

<210> SEQ ID NO 27
<211> LENGTH: 22
<212> TYPE: PRT
<213> ORGANISM: artificial sequence
<220> FEATURE:
<223> OTHER INFORMATION: fusion protein

<400> SEQUENCE: 27

Ile Ile Ser Trp Val Ile Gly Met Asp Asp Ala Gly Arg Lys Lys Arg
1               5                   10                  15

Arg Gln Arg Arg Arg Cys
            20
```